United States Patent [19]
Granneman et al.

[11] Patent Number: 5,364,772
[45] Date of Patent: Nov. 15, 1994

[54] DNA MOLECULE ENCODING THE $\beta_3$-ADRENERGIC RECEPTOR

[75] Inventors: James G. Granneman, Troy; Kristine N. Lahners, Grosse Pointe Woods, both of Mich.; Donald D. Rao, Chicago, Ill.

[73] Assignee: Wayne State University, Detroit, Mich.

[21] Appl. No.: 916,901

[22] Filed: Jul. 20, 1992

[51] Int. Cl.$^5$ .............................................. C12N 15/12
[52] U.S. Cl. ................................. 435/69.1; 435/240.2; 435/320.1; 435/172.1; 536/23.1
[58] Field of Search .................. 536/23.1; 435/69.1, 435/240.2, 320.1, 6, 172.1

[56] References Cited

U.S. PATENT DOCUMENTS 5,288,607  2/1994  Emorine ................................. 435/6

FOREIGN PATENT DOCUMENTS 9008775  8/1990  France .

OTHER PUBLICATIONS

J. Arch et al., Nature 309, 1984, 163–165.
L. Emorine et al., Sci. 245, 1989, 1118–1120.
L. Emorine et al., Biochem. Pharm. 41, 1991, 853–859.
L. Emorine et al., Am. J. Clin. Nutr. 55, 1992, 215S–218S.
C. Nahmias et al., EMBO Journal 10, 1991, 3721–3727.
Ross et al., 1990 Proc. Natl. Acad. Sci., 87, 9590–9594.
Muzzin et al., 1991, J. Biol. Chem., 266, 24053–24058.
Granneman et al., 1991, Mol. Pharm., 40, 895–899.
Brooks et al., 1991, J. Biol. Chem., 266, 7848–7859.
Hutchinson et al., 1978, J. Biol. Chem., 253, 6551.

*Primary Examiner*—Robert J. Hill, Jr.
*Assistant Examiner*—Sally P. Teng
*Attorney, Agent, or Firm*—Reising, Ethington, Barnard, Perry & Milton

[57] ABSTRACT

Described herein is the $\beta_3$-adrenergic receptor protein and DNA which encodes the protein, vectors containing the DNA, host cells transformed with the vectors and methods of using the protein, the DNA and the transformed host cells.

12 Claims, 14 Drawing Sheets

```
         10              20              30              40
         |               |               |               |
ATG GCT CCG TGG CCT CAC GAG AAC AGC TCT CTT GCC CCA TGG CCG
MET Ala Pro Trp Pro His Glu Asn Ser Ser Leu Ala Pro Trp Pro 50              60              70              80              90
         |               |               |               |               |
GAC CTC CCC ACC CTG GCG CCC AAT ACC GCC AAC ACC AGT GGG CTG
Asp Leu Pro Thr Leu Ala Pro Asn Thr Ala Asn Thr Ser Gly Leu 100             110             120             130
         |               |               |               |
CCA GGG GTT CCG TGG GAG GCG GCC CTA GCC GGG GCC CTG CTG GCG
Pro Gly Val Pro Trp Glu Ala Ala Leu Ala Gly Ala Leu Leu Ala 140             150             160             170             180
         |               |               |               |               |
CTG GCG GTG CTG GCC ACC GTG GGA GGC AAC CTG CTG GTC ATC GTG
Leu Ala Val Leu Ala Thr Val Gly Gly Asn Leu Leu Val Ile Val 190             200             210             220
         |               |               |               |
GCC ATC GCC TGG ACT CCG AGA CTC CAG ACC ATG ACC AAC GTG TTC
Ala Ile Ala Trp Thr Pro Arg Leu Gln Thr MET Thr Asn Val Phe 230             240             250             260             270
         |               |               |               |               |
GTG ACT TCG CTG GCC GCA GCC GAC CTG GTG ATG GGA CTC CTG GTG
Val Thr Ser Leu Ala Ala Ala Asp Leu Val MET Gly Leu Leu Val 280             290             300             310
         |               |               |               |
GTG CCG CCG GCG GCC ACC TTG GCG CTG ACT GGC CAC TGG CCG TTG
Val Pro Pro Ala Ala Thr Leu Ala Leu Thr Gly His Trp Pro Leu 320             330             340             350             360
         |               |               |               |               |
GGC GCC ACT GGC TGC GAG CTG TGG ACC TCG GTG GAC GTG CTG TGT
Gly Ala Thr Gly Cys Glu Leu Trp Thr Ser Val Asp Val Leu Cys
```

Fig-1A

```
           370              380              390              400
            |                |                |                |
GTG ACC GCC AGC ATC GAA ACC CTG TGC GCC CTG GCC GTG GAC CGC
Val Thr Ala Ser Ile Glu Thr Leu Cys Ala Leu Ala Val Asp Arg 410              420              430              440              450
      |                |                |                |                |
TAC CTG GCT GTG ACC AAC CCG CTG CGT TAC GGC GCA CTG GTC ACC
Tyr Leu Ala Val Thr Asn Pro Leu Arg Tyr Gly Ala Leu Val Thr 460              470              480              490
            |                |                |                |
AAG CGC TGC GCC CGG ACA GCT GTG GTC CTG GTG TGG GTC GTG TCG
Lys Arg Cys Ala Arg Thr Ala Val Val Leu Val Trp Val Val Ser 500              510              520              530              540
      |                |                |                |                |
GCC GCG GTG TCG TTT GCG CCC ATC ATG AGC CAG TGG TGG CGC GTA
Ala Ala Val Ser Phe Ala Pro Ile MET Ser Gln Trp Trp Arg Val 550              560              570              580
            |                |                |                |
GGG GCC GAC GCC GAG GCG CAG CGC TGC CAC TCC AAC CCG CGC TGC
Gly Ala Asp Ala Glu Ala Gln Arg Cys His Ser Asn Pro Arg Cys 590              600              610              620              630
            |                |                |                |                |
TGT GCC TTC GCC TCC AAC ATG CCC TAC GTG CTG CTG TCC TCC TCC
Cys Ala Phe Ala Ser Asn MET Pro Tyr Val Leu Leu Ser Ser Ser 640              650              660              670
            |                |                |                |
GTC TCC TTC TAC CTT CCT CTT CTC GTG ATG CTC TTC GTC TAC GCG
Val Ser Phe Tyr Leu Pro Leu Leu Val MET Leu Phe Val Tyr Ala 680              690              700              710              720
            |                |                |                |                |
CGG GTT TTC GTG GTG GCT ACG CGC CAG CTG CGC TTG CTG CGC GGG
Arg Val Phe Val Val Ala Thr Arg Gln Leu Arg Leu Leu Arg Gly 730              740              750              760
            |                |                |                |
GAG CTG GGC CGC TTT CCG CCC GAG GAG TCT CCG CCG GCG CCG TCG
Glu Leu Gly Arg Phe Pro Pro Glu Glu Ser Pro Pro Ala Pro Ser
```

Fig-1B

```
        770                 780                 790                 800                 810
         |                   |                   |                   |                   |
CGC TCT CTG GCC CCG GCC CCG GTG GGG ACG TGC GCT CCG CCC GAA
Arg Ser Leu Ala Pro Ala Pro Val Gly Thr Cys Ala Pro Pro Glu 820                 830                 840                 850
                     |                   |                   |                   |
GGG GTG CCC GCC TGC GGC CGG CGG CCC GCG CGC CTC CTG CCT CTC
Gly Val Pro Ala Cys Gly Arg Arg Pro Ala Arg Leu Leu Pro Leu 860                 870                 880                 890                 900
         |                   |                   |                   |                   |
CGG GAA CAC CGG GCC CTG TGC ACC TTG GGT CTC ATC ATG GGC ACC
Arg Glu His Arg Ala Leu Cys Thr Leu Gly Leu Ile MET Gly Thr 910                 920                 930                 940
                     |                   |                   |                   |
TTC ACT CTC TGC TGG TTG CCC TTC TTT CTG GCC AAC GTG CTG CGC
Phe Thr Leu Cys Trp Leu Pro Phe Phe Leu Ala Asn Val Leu Arg 950                 960                 970                 980                 990
         |                   |                   |                   |                   |
GCC CTG GGG GGC CCC TCT CTA GTC CCG GGC CCG GCT TTC CTT GCC
Ala Leu Gly Gly Pro Ser Leu Val Pro Gly Pro Ala Phe Leu Ala 1000                1010                1020                1030
                     |                   |                   |                   |
CTG AAC TGG CTA GGT TAT GCC AAT TCT GCC TTC AAC CCG CTC ATC
Leu Asn Trp Leu Gly Tyr Ala Asn Ser Ala Phe Asn Pro Leu Ile 1040                1050                1060                1070                1080
         |                   |                   |                   |                   |
TAC TGC CGC AGC CCG GAC TTT CGC AGC GCC TTC CGC CGT CTT CTG
Tyr Cys Arg Ser Pro Asp Phe Arg Ser Ala Phe Arg Arg Leu Leu 1090                1100                1110                1120
                     |                   |                   |                   |
TGC CGC TGC GGC CGT CGC CTG CCT CCG GAG CCC TGC GCC GCC GCC
Cys Arg Cys Gly Arg Arg Leu Pro Pro Glu Pro Cys Ala Ala Ala 1130                1140                1150                1160                1170
         |                   |                   |                   |                   |
CGC CCG GCC CTC TTC CCC TCG GGC GTT CCT GCG GCC CGG AGC AGC
Arg Pro Ala Leu Phe Pro Ser Gly Val Pro Ala Ala Arg Ser Ser
```

Fig-1C

```
                1180            1190            1200            1210
                 |               |               |               |
        CCA GCG CAG CCC AGG CTT TGC CAA CGG CTC GAC GGG GCT TCT TGG
        Pro Ala Gln Pro Arg Leu Cys Gln Arg Leu Asp Gly Ala Ser Trp

1220
             |
        GGA GTT TCT TAG
        Gly Val Ser ---
```

Fig-1D

EXON 1

Pro Ala Ser Pro Val Ala Ser Arg Gln Asn Ser Pro Leu Asn Ar
       CCA GCT AGC CCT GTT GCG TCC AGG CAG AAC TCA CCG CTC AAC AG

GTAGGCGACGCAGGCAGAGGACTGGAGTCTGGGTGGGGACGCCTCTGTCTCTATTTTTGAGTTTG
AGGGTTGGGGGAGGAGAAGGTGTAGACAGGGCTTTTGTCTCGAGAGGACAGAAAAGGAGTAAGAA
CAGAATCGGGATCTAGGGCCCTTCCTTTTATTGGATCCAATCCCTGGGTCTGAGGCAAAGGAGGA
AAGGGAAATTTGTTCACCTTGGGACCAGGTGAGCCCCACAGGTTTCTGCCAGCAGGTTTCTGACC
TCTCTGGTTGCCTCTAGTTTGGATCTTTTTAGTTCTATTCTCCAGGCGCCCAGGTATCACTAACT
TGTCTGGGACATCCATAGACAGCAATGGACATGTCAAGTCCTCTGCCTCAGTTCCGCTTTCTTTC
AA<u>AG</u>

EXON 2 g Phe Asp Gly Tyr Glu Gly Glu Arg Pro Phe Pro Thr ---
      G TTT GAT GGC TAT GAA GGT GAG CGT CCA TTT CCC ACA TGA

AGGACCATGGAGATCTAGCAAGGAGCCT

<u>GT</u>GAGTTGAATTTGAGCTGCTTTTCTCCCTCAGGGACTGGATTCGAGGTGTAGGGTGGGATGAGG
GAGGGTGCAGGATGATCCCTATATCTTTGAAAAGTAAATATGCTATTCAGGGTTCCTGAGTCACT
CCCCTCTTACCTCCAGTGCTTGATCCGCACCTCCTTGACTGGTTACCCCAAGAAATATTGTTTCC
GTTTTGC<u>AG</u>

EXON 3

GACTTCTGGAGAAATTTTTTTTTAAGACAGAAAGA...

Fig-2C

```
              GENOMIC                              cDNA

Rat     CCG CTC AAC AGG TAG          CCG CTC AAC AGG TTT GAT GGC TAT GAA
        Pro Leu Asn Arg              Pro Leu Asn Arg Phe Asp Gly Tyr Glu

GGT GAG CGT CCA TTT CCC ACA TGA
                                     Gly Glu Arg Pro Phe Pro Thr STOP
```

Fig-5a

```
Mouse   CCG CTC AAC AGG TAG
        Pro Leu Asn Arg
```

Fig-5b

```
Human   CGG CTC GAC GGG TAG
        Arg Leu Asp Gly
```

Fig-5c

...GTT GAA GCC AGG CAG AGT CCA CCG CTC AAC AGG TTT GAT GGC TAT
   Val Glu Ala Arg Gln Ser Pro Pro Leu Asn Arg Phe Asp Gly Tyr

GAA GGT GCG CGT CCG TTT CCC ACG TGA AGGGCCGTGAAGATCCAGCAAG
   Glu Gly Ala Arg Pro Phe Pro Thr ---

GAAGCTGACTTCTGGGGATTTTTTTTTTCCTCCAGAAAGACAAGCAACGTCCAT...

Fig-6

(162 bp to begining of clone)... GCG CAG CCC AGG CTT TGC CAA
                                  Ala Gln Pro Arg Leu Cys Gln CGG CTC GAC GGG GCT TCT TGG GGA GTT TCT TAG GCCTGAAGGACAAGAA
Arg Leu Asp Gly Ala Ser Trp Gly Val Ser ---

GCAACAACTCTGTTGATCAGAACCTGTGGAAA...(680 bp to poly A)

Fig-10A

| | | | | |
|---|---|---|---|---|
| AATTCTGCCT | TCAACCCGCT | CATCTACTGC | CGCAGCCCGG | ACTTTCGCAG |
| CGCCTTCCGC | CGTCTTCTGT | GCCGCTGCGG | CCGTCGCCTG | CCTCCGGAGC |
| CCTGCGCCGC | CGCCCGCCCG | GCCCTCTTCC | CCTCGGGCGT | TCCTGCGGCC |
| CGGAGCAGCC | CAGCGCAGCC | CAGGCTTTGC | CAACGGCTCG | ACGGGGCTTC |
| TTGGGGAGTT | TCTTAGGCCT | GAAGGACAAG | AAGCAACAAC | TCTGTTGATC |
| AGAACCTGTG | GAAAACCTCT | GGCCTCTGTT | CAGAATGAGT | CCCATGGGAT |
| TCCCCGGCTG | TGACACTCTA | CCCTCCAGAA | CCTGACGACT | GGGCCATGTG |
| ACCCAAGGAG | GGATCCTTAC | CAAGTGGGTT | TTCACCATCC | TCTTGCTCTC |
| TGTCTGAGAG | ATGTTTTCTA | AACCCCAGCC | TTGAACTTCA | CTCCTCCCTC |
| AGTGGTAGTG | TCCAGGTGCC | GTGGAGCAGC | AGGCTGGCTT | TGGTAGGGGC |
| ACCCATCACC | CGGCTTGCCT | GTGCAGTCAG | TGAGTGCTTA | GGGCAAAGAG |
| AGCTCCCTG | GTTCCATTCC | TTCTGCCACC | CAAACCCTGA | TGAGACCTTA |
| GTGTTCTCCA | GGCTCTGTGG | CCCAGGCTGA | GAGCAGCAGG | GTAGAAAAGA |
| CCAAGATTTG | GGGTTTTATC | TCTGGTTCCC | TTATTACTGC | TCTCAAGCAG |
| TGGCCTCTCT | CACTTTAGCC | ATGGAATGGC | TCCGATCTAC | CTCACAGCAG |
| TGTCAGAAGG | ACTTCGCCAG | GGTTTTGGGA | GCTCCAGGGT | TCATAAGAAG |
| GTGAACCATT | AGAACAGATC | CCTTCTTTTC | CTTTTGCAAT | CAGATAAATA |
| AATATCACTG | AATGCAGTTC | | | |

Fig-10B

DNA MOLECULE ENCODING THE β3-ADRENERGIC RECEPTOR

GRANT REFERENCE

The research carried out in connection with this invention was supported in part by a grant from the NIH (DK37006).

FIELD OF INVENTION

The present invention relates to $\beta_3$-adrenergic receptor protein, DNA encoding the protein, the genetic elements controlling expression of the gene, and the use of host cells transformed with DNA encoding the protein for screening compounds having utility in modulating the activity of the $\beta_3$-adrenergic receptor.

BACKGROUND OF THE INVENTION

The human $\beta_3$-adrenergic receptor ($\beta_3$ receptor) gene was discovered in 1989 (L. J. Emorine et al., Sci. 245, 1989, 1118–1120). The $\beta_3$ receptor protein is widely considered to be a target for agents that will be useful as human therapeutics (J. R. S. Arch et al., Nature 309, 1984, 163–165), as well as for agents that beneficially alter the meat and fat content of feed animals. It has been believed and repeatedly published by those that originally described the $\beta_3$ receptor gene that the rodent and human $\beta_3$ receptor genes were intronless and that the human gene contained a single exon that encoded a protein of 402 amino acids (Emorine et al., ibid; L. J. Emorine et al, Biochem. Pharmacology 41, 1991, 853–859; L. J. Emorine et al., Am. J. Clin. Nutr. 55 1992, 215S–218S; and C. Nahmias et al. EMBO Journal 10, 1991, 3721–3727). DNA constructs have been made that are based upon the assumption that the human $\beta_3$ receptor gene contains only 402 amino acids, and these constructs have demonstrated commercial value as reagents for the development of compounds that specifically interact with the $\beta_3$ receptor protein.

We have discovered that the assumption that the human $\beta_3$ receptor gene contains only one protein-coding block is incorrect. Specifically, we have discovered that the human, rat and mouse $\beta_3$ receptor genes contain two protein-coding exons. Thus, the amino acid sequence of the human and mouse $\beta_3$-adrenergic receptor proteins that were previously deduced from genomic DNA are incomplete. Most significantly, we have discovered that the human $\beta_3$ receptor gene is 6 amino acids larger than previously believed. Because we have cloned the human receptor cDNA, we have, for the first time, elucidated the correct amino acid sequence of the human $\beta_3$ receptor. (SEQ. ID. NO. 1)

DESCRIPTION OF THE FIGURES

FIG. 1A–D. Shows the full coding sequence for the human $\ominus_3$-adrenergic receptor sequence and the deduced amino acid. (SEQ. ID. NO. 1)

FIG. 2A–C. The structure of the full-length rat $\beta_3$ receptor gene, (SEQ. ID. NO. 7) (A) restriction enzyme map illustrating the locations of restriction enzyme cleavage sites and the transition initiation (ATG) and termination (TGA) codons (B) is a schematic representation of the rat $\beta_3$ receptor gene, with mature mRNA blocked and the coding sequence filled (E, exon; I, intron), (C) lists nucleic acid and amino acid sequences of exon/intron junctions of the rat $\beta_3$ receptor gene, beginning with Pro$^{374}$, donor and acceptor splice sites underlined, inverted repeat with NF-1 homology in bold.

FIG. 5A–C. Comparison of the mouse and human $\beta_3$ receptor gene sequences with the homologous sequence of the first exon/intron junction in the rat gene. Underlined are donor splice signals; the translation termination codons proposed by Emorine et al. (1989, ibid) and Nahmias et al. (1991, ibid) are in bold (A) rat genomic and cDNA sequence, (B) mouse genomic sequence, (C) human genomic sequence.

FIG. 6. The nucleic acid and deduced amino acid sequences of a partial mouse $\beta_3$ receptor CDNA. )(SEQ. ID. NO. 8)

FIG. 9A–C. RNase protection analysis of human $\beta_3$ receptor mRNA expressed in SK-N-MC cells (A) is a diagrammatic representation of p174 and (B) is an autoradiograph of probe fragments protected from nuclease digestion.

FIG. 10A–B. Nucleotide and amino acid sequence of a partial human $\beta_3$ receptor cDNA (p184). FIG. 10B shows the entire partial sequence (SEQ. ID. NO. 3) and FIG. 10A shows the portion containing the second exon.

SUMMARY OF THE INVENTION

Figure 2A:
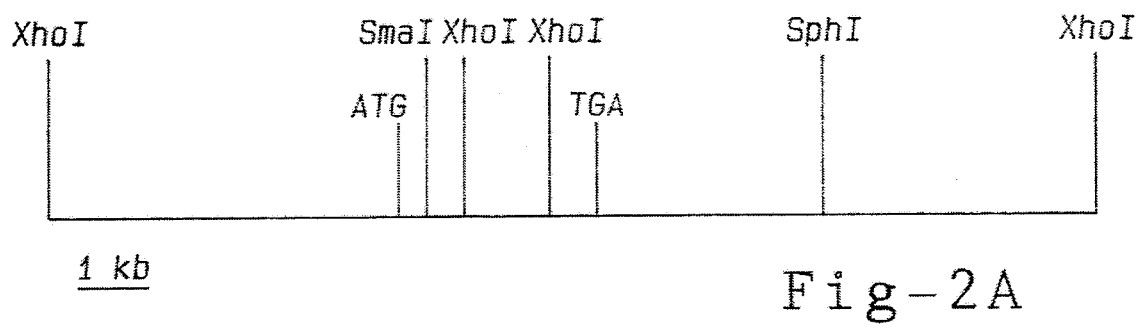

The present invention provides the $\beta_3$-adrenergic receptor protein and DNA which expresses the protein. We have found as described in detail below that previous reports indicating that human $\beta_3$-adrenergic receptor protein is 402 amino acids in length are erroneous and, in fact, the protein is 408 amino acids (SEQ. ID. NO. 2) in length which provides the basis of the present invention.

The present invention also provides a means for transforming a host cell with a vector containing the DNA which expresses the $\beta_3$-adrenergic receptor and methods of using the transformed host cell for detecting agents, such as chemical compounds, which affect the activity of the protein.

In another embodiment of the invention, there is provided a means for modifying the DNA which expresses the β3-adrenergic receptor protein by site-directed mutagenesis to eliminate a donor splice site to avoid expression of fusion proteins.

Another embodiment of the invention provides oligonucleotide probes which are useful in detecting the presence of mRNA specific for the β3-adrenergic receptor protein in cells.

The present invention further provides DNA constructs comprising fat-specific elements of mammalian DNA which expresses β3-adrenergic receptor proteins.

Additionally, there is provided novel monoclonal antibodies to the β3-adrenergic receptor and fragments thereof.

DETAILED DESCRIPTION OF THE INVENTION

In carrying out the work described herein, the following procedures were employed:

General recombinant DNA methods

Standard cloning techniques used are described by Maniatis et al. (Molecular Cloning: A Laboratory Manual, 1982, Cold Spring Harbor Laboratory, Cold Spring Harbor, N.Y.). RNA extraction, reverse transcription of tissue RNA and polymerase chain reaction amplification were performed as previously described by Granneman et al. (Endocrinology 130, 1992, 109–114).

Generation of β3 cDNA probes.

Probes for cloning the rat β3 receptor cDNA and for measurement of tissue mRNA were obtained with the PCR. Brown adipose tissue (BAT) RNA (10 μg) was reverse-transcribed with a β receptor-specific (Emorine et al., 1989, ibid; Kobilka et al., Proc. Natl. Acad. Sci. 84, 1970, 46–50; and Frielle et al., Proc. Natl. Acad. Sci 84, 1987, 7920–7924) oligonucleotide, primer A, 5'-GCGAATTCGAAGGCAC-TICIGAAGTCGGGGCTGCGGCAGTA-3', which also contained an EcoRI restriction site on the 5' end. This cDNA was then amplified with primer A and the human β3-specific primer 5'-GCGCTGCGCCCGGACAGCTGTGGTCCTGG-3' (Emorine et al, 1989, ibid). PCR was performed as described previously by Innis et al. (PCR Protocols, Acad. Press, San Diego, 1990, 54–59). Samples were denatured for 2 min at 94°, annealed, and extended at 72° for 4 mn. Thirty rounds of amplification were performed. One microliter of this reaction was further amplified, described above, with the β3-specific primer described above and a downstream primer, 5'-GCGAATTCGAAGAAGGGCAGCCAGCAGAG-3', that is common (except for the added EcoRI site) to all β receptors (Emorine et al., 1989, ibid; Kobilka et al., 1970, ibid; and Frielle et al., 1987, ibid). The β3 receptor PCR product was cloned into the SmaI and EcoRI sites of the plasmid pGEM 3Z (Promega) and sequenced by the dideoxynucleotide chain-termination technique (Sequenase; United States Biochemical Corp). The PCR product was found to be highly homologous to the human β3 receptor gene (Emorine et al., 1989, ibid) and, ultimately, identical to a rat cDNA clone encoding the rat β receptor.

Library construction and screening (rat)

Library construction, screening, and cloning were performed using standard techniques (Maniatis et al., 1982, ibid). A cDNA library was constructed in LambdaGEM-4 (Promega) using poly(A)+RNA isolated from BAT of cold-exposed rats. This library contained approximately $3 \times 10^6$ recombinants, with an average insert size of 1.5 kb. Three hundred thousand recombinants were screened at high stringency (0.03M NaCl, 3 mM sodium citrate, pH 7, at 55°) with the cloned rat β3 PCR product labeled with ($^{32}$P)dCTP using random primers (Maniatis et al., ibid). Twenty-seven phage were isolated from the amplified library, and two plasmids (p108 and p109) of the same size (about 1.73 kb) were rescued. Sequencing of p108 and p109 from the 5' ends indicated they were identical and truncated with respect to the predicted initiation codon of the human β3 receptor sequence (Emorine et al., 1989, ibid). Screening of the remaining isolates by PCR failed to detect any full-length cDNAs, and primer extension experiments with tissue mRNA suggested that secondary structure, owing to high G-C content, may have limited the ability of the reverse transcriptase to synthesize cDNA through the missing 5' region. Therefore, to obtain the remaining sequence, a Sprague-Dawley rat genomic library (Clontech) was screened with a p108 probe to obtain the rat genomic sequence. The rat β3 gene (FIG. 2 gives complete sequence) was identified by sequencing four hundred forty-four base pairs of genomic sequence that overlapped with p108 β3 receptor DNA. A full-length clone was then produced by cloning the genomic sequence from bases −104 to +390 (relative to translation initiation) into the AccI site of p108. Both DNA strands were sequenced by the dideoxy chain-termination technique (Maniatis et al., ibid), and no discrepancies were found.

Transfection of CHO-k1 cells

The assembled β3 receptor construct was cloned into pRC/CMV (Invitrogen), an expression vector containing the cytomegalovirus promoter and a neomycin resistance gene. This construct was transfected into CHO-k1 cells using the CaPO4 method. Stably transfected cells were selected in the presence of Geneticin (800 μg/ml) and pooled for further analysis.

Numerous eucaryotic cells can be used. Preferably, these cells will not express any related β adrenergic receptor (i.e., $β_1$, $β_2$, or $β_3$ receptors). Examples of such cells include Chinese hamster ovary cells, murine B-82 cells, murine adrenal cortical Y1 cells, xenopus oocytes, or insect Sf cells.

Numerous vectors, some with promoters that are geared to specific cell types can be used. Examples are inducible promoters like mouse mammary tumor virus (MMTV) promoter or metalothionin promoter. Others include retrovirus vectors for gene therapy. Based upon the information in Example 1 below, numerous variations are possible.

Adenylyl cyclase assay

Adenylyl cyclase activity was determined by the method of Salomon (Adv. Cyclic Nucleotide Res. 10, 1979, 35–55). Culture medium was removed and cells were washed in phosphate-buffered saline and then harvested in 25 mM HEPES (pH 8.0) buffer containing 2 mM MgCl$_2$ and 1 mM EDTA. Cell were homogenized and centrifuged at 48,000×g for 15 min. to obtain crude membranes. Membrane pellets were resuspended and used directly or frozen at −80° until used. Freezing did not affect activity. Membranes (5–15 μg of protein) were preincubated at 4°, in a volume of 40 μl, with the specified drugs for 15 min. Adenylyl cyclase reactions were initiated by addition of substrate mixture and were terminated after 30 min at 30°. BAT membrane adenylyl cyclase activity was determined as previously described (Granneman et al., J. Pharmacol. Exp. Ther. 254, 1990, 508–513, and Granneman et al., J. Pharmacol. Exp. Ther. 256, 1991, 412–425), using membranes from 7-day-old rats. Concentration-response data were analyzed by nonlinear regression analysis with a one-site mass action equation for transfected CHO cells (Enzfitter, Elsevier Biosoft). A two-site model was used to analyze catecholamine-stimulated adenylyl cyclase in BAT, with the low affinity component representing stimulation by $\beta_3$ receptors (Chaudhry et al., Am. Jour. Physiol. 261, 1991, R403–R411).

Tissue mRNA analysis

The size of the $\beta_3$ receptor transcripts was determined by Northern blot analysis of rat poly(A)+RNA, as previously described (Maniatis et al., ibid; and Granneman et al., Endocrinology 125, 1989, 2328–2335). The cDNA probe used corresponded to bp 228–665 of FIG. 1A-B (SEQ. ID. NO. 1)and was labeled by random primers. Tissue mRNA distribution experiments were conducted on total RNA with a solution hybridization assay (Maniatis et al., ibid; and Granneman et al., Endocrinology 127, 1990, 1596–1601). The radioactive cRNA probe used was transcribed in Vitro from the cloned $\beta_3$ receptor PCR product (p101) with [$^{32}$P]CTP, using the T7 promoter. The probe corresponded to bp 746–917 in FIG. 1B–C. Tissue or cellular RNA (6–50 $\mu$g) was co-precipitated with $3 \times 10^4$ cpm of the $^{32}$P-labeled cRNA probe. Samples were hybridized at 55° for 12–18 hr and then diluted, and the nonhybridized probe was digested with 300 units of T-1 ribonuclease for 45 min at 37°. The [$^{32}$P]RNA probe that was protected from RNase digestion was electrophoretically resolved on a denaturing polyacrylamide gel containing 8M urea. The gels were dried and exposed to Kodak XAR-5 film for 18–72 hr.

Analysis of $\beta_3$ receptor mRNA by RNase protection assay.

Rat and human $\beta_3$ receptor mRNAs were analyzed by RNase protection assay using species-specific probes. The rat probe used (p152) was the BssHII to BglII fragment of the cloned rat $\beta_3$ cDNA cloned into pGEM-7z. This sequence (SEQ. ID. NO. 7) spans the first exon/intron junction.

Human mRNA was mapped with a $\beta_1$ receptor probe and two $\beta_3$ receptor probes that were amplified from human genomic DNA. A $\beta_3$ receptor (p146) and the $\beta_1$ (p145) probes were amplified by "nested" PCR (Granneman et al. Molecular Pharmacol. 40, 1991, 895–899) from total nucleic acids using primers based upon the published sequences (Emorine et al., 1989, ibid and Frielle et al., 1987, ibid). The resulting receptor DNAs were shortened and cloned into pGEM-7z for the generation of riboprobes. These probes are exact matches of the published sequences and encode amino acids 178–271 ($\beta_1$) and 151 to 223 ($\beta_3$). The second human $\beta_3$ receptor probe was amplified from genomic DNA (Promega) with a primer set that was designed to amplify a 256 bp DNA fragment which spanned the putative donor splice site. The coding strand primer (HB3G+) was 5'TGCGAATTCTGCCTT-CAACCCGCTC 3' and the noncoding strand primer was 5' GCAGGATCCACGGACACATC-GCATGCTTCC 3'. Both primers were based upon the published human sequence and contained engineered restriction sites of the 5' ends for cloning into pGEM-7z (p174). The sequence of p174 was an exact match of the published human $\beta_3$ receptor gene sequence except for a discrepancy of A for G in the published sequence at bp 1193 (GenBank accession #M29932). This potential discrepancy does not affect the nuclease protection assay because the T-1 ribonuclease used does not cleave at A (J. N. Davidson, The Biochem. of Nucleic Acids, 7th ed., 1972, Academic Press, New York), and no fragments indicative of cleavage at this site were detected.

Cloning of a partial mouse $\beta_3$receptor cDNA

The mouse $\beta_3$ receptor cDNA was obtained from mouse white adipose tissue RNA by reverse transcription/PCR (Granneman et al., 1992, ibid). Reverse transcription of total RNA was performed with the oligonucleotide primer 5' ATTAAAAGGTTTGCATC 3' that was based upon the rat cDNA (Granneman et al., 1991, ibid). The resulting cDNA was then amplified by PCR. The coding strand primer was 5' GGACTTTCG-CGACGCCT 3' and the noncoding strand primer was 5' GCATCCATGGACGTTGCTTGTC 3', which were also based upon the rat sequence. Samples were denatured at 94° C. for 2 min., annealed at 63° C. for 1.5 min and extended at 72° C. for 2 min for 30 cycles. The resulting PCR product was shortened to 180 bp, cloned into pGEM-7z (p158) and sequenced.

PCR analysis of mouse and rat genomic DNA

To estimate the size of the mouse intron(s), PCR analysis was conducted on mouse and rat genomic DNA. The primer set used was the same that was used above to amplify the mouse cDNA. PCR was carried out for 30 cycles using 1 $\mu$g of mouse or rat genomic DNA (Promega) as described above. PCR products were resolved on 1% agarose gel containing ethidium bromide and visualized with ultraviolet light. The identity of these products was verified by Southern blot analysis with an internal probe from the rat cDNA.

Cell culture

SK-N-MC cells were grown in Dulbecco's modified Eagle's medium containing 10% fetal calf serum (Hyclone), penicillin (100,000 units/l) and streptomycin (100 mg/l). Cells were subcultured at a ratio of 1:10 and harvested when about 80% confluent.

Mammalian tissues

Rat tissues were obtained from male Sprague-Dawley rats and mouse tissues were from male outbred mice (Hilltop Labs). Human adipose tissue was obtained with informed consent from surgical specimens.

The discovery of the authentic amino acid sequence (SEQ. ID. NO. 1) of the human $\beta$-adrenergic receptor represents a significant improvement in the state of the art with respect to technologies surrounding the $\beta_3$ receptor. Specifically, cells expressing the correct amino acid sequence will be most preferable to screen agents for human and animal use. The full length (408 amino acids) human $\beta_3$-adrenergic receptor (SEQ. ID. NO. 2) we have discovered has a pharmacological profile that is different from the truncated (402 amino acids) receptor previously reported. Pindolol derivatives and BRL3744 are partial agonists at both the full length and truncated receptors. However, there is a dramatic difference in the differential potency of typical $\beta$-adrenergic receptor antagonists. Propranolol and alprenolol inhibit the full length receptor with submicromolar potencies, but have been reported to be essentially inactive at the truncated receptor (Emorine et al., 1989, ibid). It is difficult to compare the potencies of agonists because of possible differences in receptor reserves, and problems in comparing data from binding and functional measurements. Based on the limited data available, however, it appears that CYP is about 100-fold less potent at the full length receptor than at the truncated receptor. Pindolol has been reported to have $EC_{50}$ values of 150 nM or 1100 nM in truncated $\beta_3$-transfected CHO cells, while we found an $EC_{50}$ of 2800 nM, although a $K_I$ of 84 nM in these cells. Similarly, the $EC_{50}$ for BRL 37344 in truncated $\ominus_3$-transfected CHO cells has been reported to be 6 nM and 180 nM, but we found it to be 840 nM in cells which produce the full-length receptor. It appears that the full-length receptor more closely resembles the "atypical" $\beta$-adrenergic receptor found in cardiac, intestinal and adipose tissues and the cloned rat $\beta_3$-receptor than the cloned human truncated $\beta_3$-receptor. Similarities include 1) a submicromolar affinity for classical $\beta$-adrenergic receptor antagonists; 2) a midnanomolar affinity for CYP; 3) activation by pindolol derivatives with low potency; and 4) a relatively low potency of BRL 37344.

The rodent $\beta_3$ receptor is abundantly expressed only in adipose tissue (Granneman et al., 1991, ibid). In this regard, the original tissue distribution of the $\beta_3$ receptor mRNA described by Emorine et al. (1989, ibid) was erroneous because most of the probe that was used was derived from the first intron and the exon sequence used had no homology with the rat tissues tested. These observations indicate that the $\beta_3$ receptor gene contains elements involved in adipose tissue-specific expression. We have isolated the rat $\beta_3$ receptor gene, (FIG. 2C) and have identified genetic elements that are likely to be involved in this phenotypic expression. Tissue-specific enhancers have been identified in the first intron of several genes (Brooks et al., J. Biol. Chem. 266, 1991, 7848-7859, and Parmacek et al., J. Biol. Chem. 265, 1990, 15970-15976). We have found the sequence within and surrounding one of the inverted repeats in the first intron of the $\beta_3$ receptor gene bears striking homology with NF-1 (Santaro et al., Natur. 334, 1988, 218-224) and with ARF6 (Graves et al., Mol. Cell. Biol. 12, 1992, 1202-1208). It is anticipated that these sequences are involved in the adipose tissue-specific expression of the $\beta_3$ receptor based on recent reports that sequences related to NF-1 and ARF6 are involved in the control of adipose tissue-specific gene expression (Graves et al., 1992, ibid. and Genes Dev. 5, 1991, 428-437). The modulation of tissue-specific genes represents a new approach in the treatment of certain diseases and in the generation of agents that produce desirable characteristics in meat-producing animals. For example, agents like Cigilazone that are being developed as antidiabetes therapeutics augment the expression of adipose tissue-specific genes (Kletzien et al., Mol. Pharmacol 41, 1992, 393-398). Efforts to identify novel agents that modify fat-specific gene expression will be facilitated greatly by cell lines expressing readily-detected reporter genes whose transcription is governed by adipose tissue-specific promoter elements. Promoter/reporter gene constructs that are based upon the fat-specific elements within the $\beta_3$ receptor gene represent a novel, useful approach for developing gene-modulating agents.

The structure of DNA sequence of the gene encoding the human $\beta_3$-adrenergic receptor and the amino acid sequence of the receptor was reported by Emorine et al. (1989, ibid). The receptor was identified by Emorine et al. as having 402 amino acids, which we have now found to be erroneous, encoded from a single exon. As noted above, we have discovered that the human $\beta_3$-adrenergic gene has two coding exons (SEQ. ID. NO. 1), and the amino acid sequence for the protein is 408 amino acids in length. (SEQ. ID. NO. 2) We have found that the TAG codon believed to be a termination codon is in a position to contain a human donor splice site (GT) as is more fully detailed below.

The discovery of the donor splice signal in the $\beta_3$-adrenergic receptor gene was initially found in the rat gene. A rat genomic library was screened with the rat $\beta_3$ receptor cDNA (SEQ. ID. NO. 5) and isolated a clone containing a 12.1 kb insert. This clone was then subjected to Southern blot analysis using the rat $\beta_3$ cDNA as a probe. Digestion of the genomic clone with Xho I revealed prominent bands of 3, 4 and 0.6 kb that hybridized to the rat $\beta_3$ receptor cDNA. Because the rat $\beta_3$ receptor cDNA (SEQ. ID. NO. 5) contains only a single Xho I site, these data suggested the existence of one or more introns in the rat $\beta_3$ receptor. Further analysis utilizing selective cDNA probes suggested the existence of intron(s) near the 3' end of the coding region. The Xho I fragments derived from the genomic clone were then isolated and sequenced.

Figure 2B:
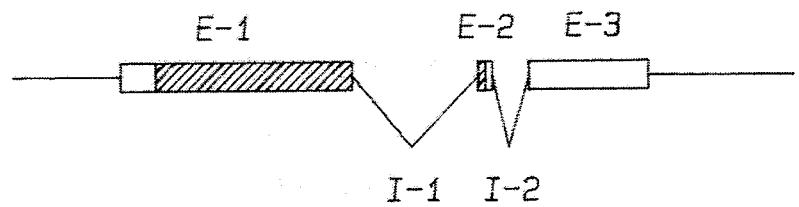

Shown in FIG. 2A is a restriction map of the rat $\beta_3$ receptor gene and the exon/intron structure of the rat $\beta_3$ receptor gene that was deduced by comparison of the genomic sequence with the cDNA (FIG. 2B). "A" shows a map of the rat $\beta_3$ receptor gene illustrating the locations of restriction enzyme cleavage sites and the translation initiation (ATG) and termination (TGA) codons. Sequences within this map are contained in the plasmids p111, p108 and p167. "B" shows a schematic representation of the rat $\beta_3$ receptor gene, with mature mRNA blocked and the coding sequence filled. E, exon; I, intron. "C" shows a nucleic acid and amino acid sequences of exon/intron junctions of the rat $\beta_3$ receptor gene, beginning with $Pro^{374}$. FIG. 2C (SEQ. ID. NO. 7) presents the last 44 nucleotides of Exon 1, Intron, Exon 2, Intron, and first 35 nucleotides of Exon 3 of the rat $\beta_3$ receptor gene. Underlined are the donor and acceptor splice sites. The inverted repeat that has homology with NF-1 is in bold. The rat $\beta_3$ receptor gene contains three exons and two introns. The first intron interrupts the open reading frame 12 amino acids from the carboxyl end (FIG. 2C). This intron is 394 bp and contains both 5' donor and 3' acceptor splicing signals. The second exon is 68 bp long and encodes the translation termination codon and 28 bp of nontranslated sequence. The second intron is 207 bp long and also contains donor and acceptor splice signals. The final exon contains sequences through the polyadenylation signal as described by Granneman et al. (Molecular Phar. 40, 1991, 895-899).

Figure 3A:
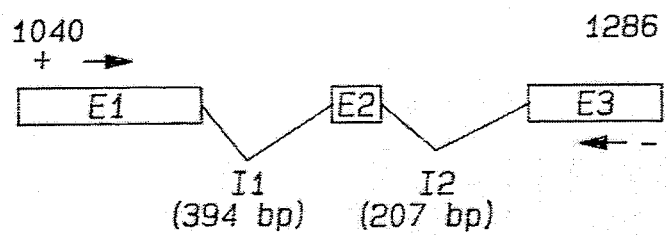
FIG. 3A–B. PCR analysis of rat $\beta_3$ receptor cDNA (SEQ. ID. NO. 5) and genomic DNA, (SEQ. ID. NO. 7) (A) is a diagram of PCR primers complementary to sequences in the first and third exons and (B) is a photograph of PCR products resolved on gels and visualized with UV light.
Figure 3B:
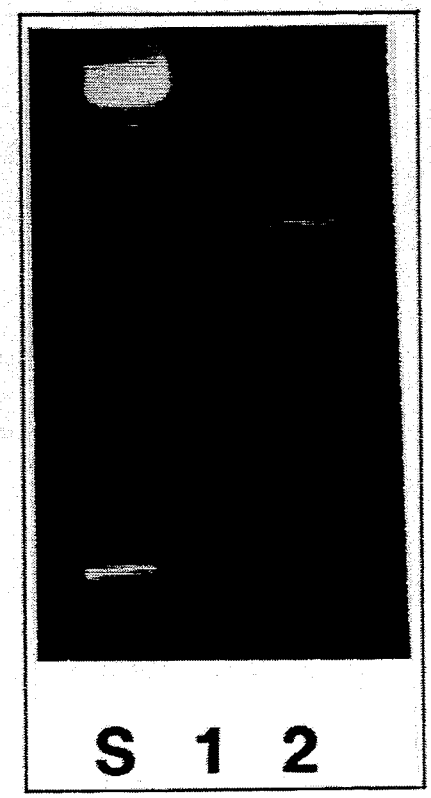
Figure 4:
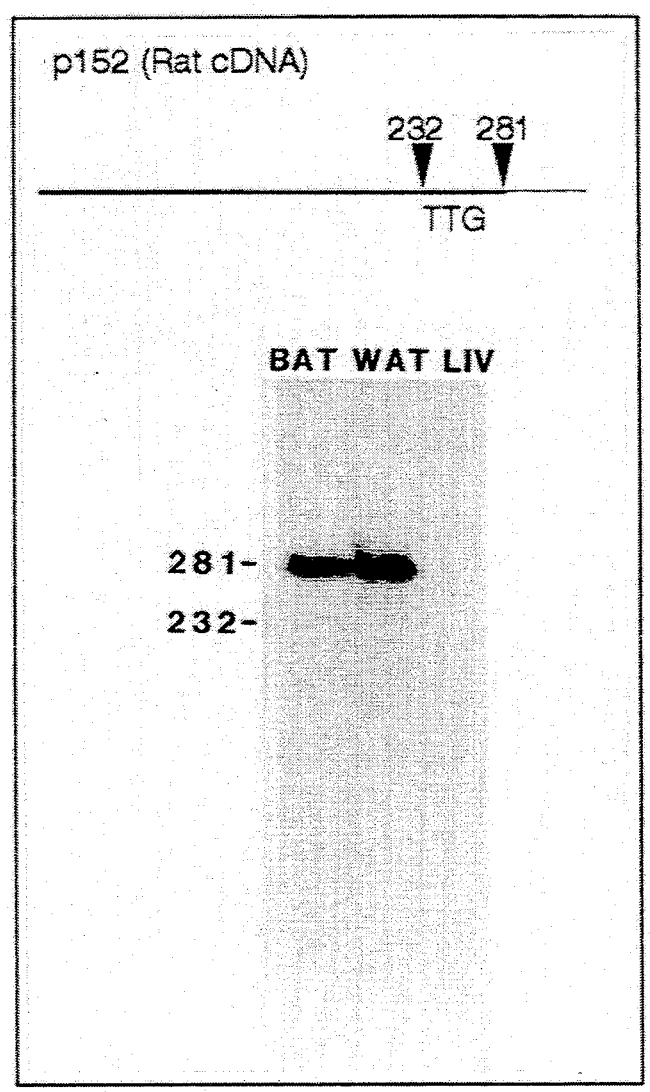
FIG. 4. Analysis of rat adipose tissue $\beta_3$ receptor mRNA by RNase protection assay. $\beta$: Location of cRNA probe relative to first exon/intron junction. B: Autoradiogram of probe protected by white (WAT), brown (BAT) adipose tissues and liver (LIV). The cRNA probe was fully protected, indicating lack of alternative splicing in these rat tissues.

To further verify that the rat $\beta_3$ receptor gene contains introns, we performed PCR analysis of rat $\beta_3$ receptor cDNA (prepared by reverse transcription of total RNA from adipose tissue) and genomic DNA. PCR primers were complementary to sequences in the first and third exons (FIG. 3A). The coding strand primer was placed upstream of the first splice junction, whereas the noncoding primer was placed in the third exon. Thus, the expected PCR product spanned the introns. As expected, this primer set amplified a 845 bp fragment from genomic DNA, as shown in lane 2 of FIG. 3B. When tissue cDNA was used as a template, the product was 246 bp (see lane 1 of FIG. 3B), as was expected if the primary transcript contained introns which had been removed. No other PCR products were observed, indicating that the $\beta_3$ pre-mRNA is not alternatively-placed. To further verify this conclusion, nuclease protection assay was performed on rat $\beta_3$ receptor mRNA. The probe used (p152) in this instance was derived from the cloned rat $\beta_3$ receptor cDNA and spanned the first exon/intron junction (FIG. 4). If both introns of the rat $\beta_3$ receptor are removed by RNA splicing, then tissue mRNA should protect the full (281 nt) complementary probe. However, if the first donor site is not used (i.e., is alternatively spliced), then a fragment of 232 nucleotides would be protected by tissue $\beta_3$ receptor mRNA. As shown in FIG. 4, RNA from both white (WAT) and brown (BAT) adipose tissues protected the full probe and no smaller fragments indicative of alternative splicing were observed. As expected, RNA from liver (LIV) failed to protect the $\beta_3$ receptor probe indicating that the expression of the gene is adipose tissue-specific (see also Granneman et al., Endocrinology 130, 1992, 109–114).

The murine and, as noted above, human $\beta_3$-adrenergic receptor genes have been cloned recently, and both were assumed to lack introns (Emorine et al., 1989, ibid, and Nahmias et al., 1991, ibid). However, analysis of the genomic sequence alone is not sufficient to decide whether this is so. As shown in FIG. 5A, the first exon/intron (SEQ. ID. NO. 5) junction of the rat gene contains the sequence AGGTAG. In the absence of information derived from cDNA, it might be concluded erroneously that the final amino acid is arginine (encoded by AGG) followed by a translation termination codon (TAG). In this regard, we noticed the sequence (FIG. 5B) of the mouse $\beta_3$ receptor gene is identical to that of the rat in this region (Nahmias et al., ibid). In addition, the human gene (FIG. 5C) also contains the sequence GGTAG in a homologous site, (SEQ. ID. NO. 1) and this sequence has been found to contain a donor splice site (GT), in which case the coding sequence continues, or it could be a termination codon (TAG), as originally deduced.

In order to verify that the mouse gene contains introns, we cloned the relevant region from mouse adipose tissue by reverse transcription of RNA followed by PCR. The nucleic acid sequence and deduced amino acid sequence of the mouse $\beta_3$ receptor cDNA is shown in FIG. 6. (SEQ. ID. NO. 8) The partial cDNA was cloned by reverse transcription of mouse adipose tissue mRNA followed by PCR. Shown is sequence beginning with the codon for Val$^{378}$. The cDNA exactly matches the genomic sequence reported by Nahmias et al. (1991, ibid) until Arg$^{388}$. The open reading frame continues for 12 more amino acids (Bold, Phe Asp Gly Tyr Glu Gly Ala Arg Pro Phe Pro Thr), which are identical to the rat sequence. The 45 bases of nontranslated sequence in this clone are 71% identical to the non-translated sequence of the rat $\beta_3$ receptor cDNA.

Figure 7:
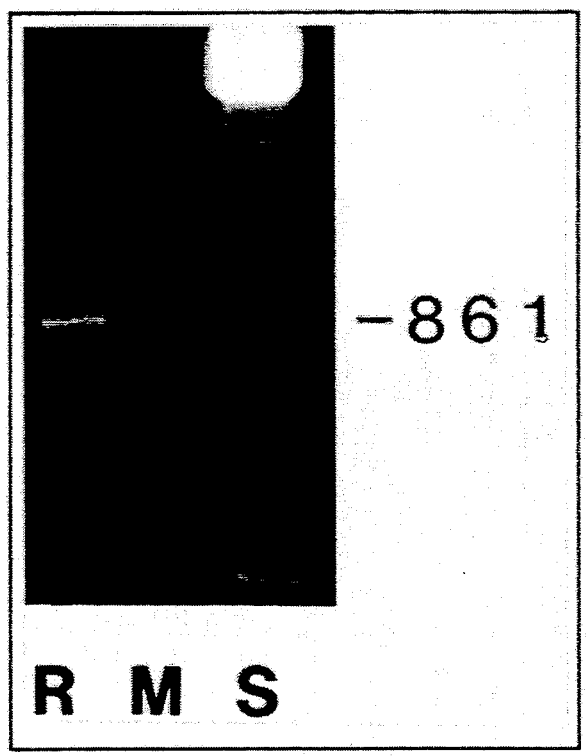
FIG. 7. PCR analysis of rat and mouse genomic DNA with cDNA-derived primers. R, rat; M, mouse. See FIG. 3 for location of PCR primers.

To further verify that the mouse $\beta_3$ receptor gene contains introns and to estimate their size, PCR analysis of genomic DNA was performed with oligonucleotide primers that were based upon cDNA and were designed to span the intron(s). In the mouse cDNA, there are 208 bp between the primers in this set. Amplification of genomic DNA with this primer set resulted in a PCR product that was about 985 bp, confirming that the mouse gene contains introns and further indicating that the intron(s) present in the mouse gene are about 120 bp larger than those in the rat gene (FIG. 7).

Figure 8:
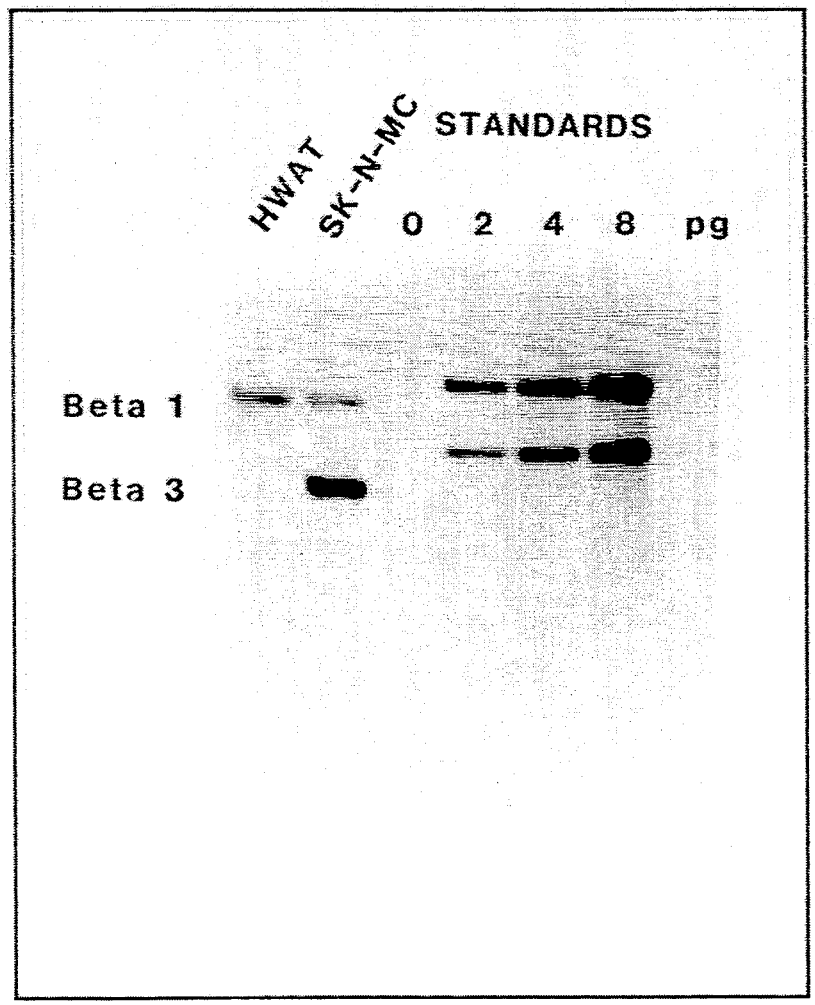
FIG. 8. Analysis of $\beta_1$ and $\beta_3$ receptor mRNA in human omental adipose tissue and in SK-N-MC cells by nuclease protection assay.

In order to determine whether the human gene contains introns, we first identified a source of human $\beta_3$ receptor mRNA for comparison. In rats, the $\beta_3$ adrenergic receptor is expressed abundantly only in adipose tissue, where $\beta_3$ receptor mRNA is about 5–7 times more abundant than $\beta_1$ receptor mRNA (Granneman et al., Endocrinology 130, 1992, 109–114). We examined mRNA from human subcutaneous and omental adipose tissues by RNAse protection assay, and although $\beta_1$ receptor mRNA could be readily detected by nuclease protection assay, transcripts encoding the $\beta_3$ receptor were absent at the detection limit of the assay (about 4 copies per cell) (FIG. 8). 50µg of total RNA was hybridized to human $\beta_1$ (p145) and $\beta_3$ (p146) receptor probes simultaneously. SK-N-MC cells contain both $\beta_1$ and $\beta_3$ receptor mRNA, while human omental adipose tissue contains only $\beta_1$ receptor transcripts. Right lane shows synthetic human $\beta_3$ receptor RNA standards. Thus, although the $\beta_3$ receptor does not appear to be expressed in human subcutaneous or omental adipose tissue, we did find that the $\beta_3$ receptor is abundantly expressed along with the $\beta_1$ receptor in the human neuroblastoma cell line SK-N-MC. Thus, these cells provide an excellent source for analysis of the human $\beta_3$ mRNA (FIG. 8).

Figure 9A:
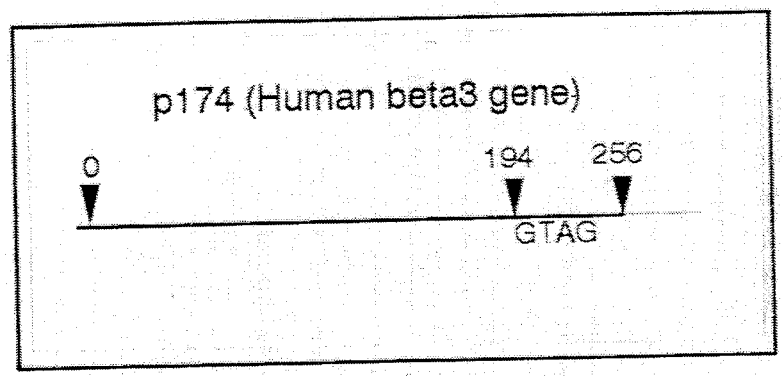
Figure 9B:
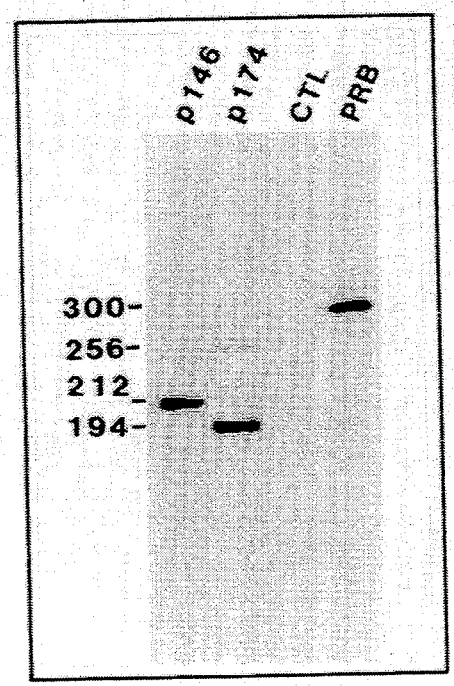

We mapped the 3' end of the $\beta_3$-adrenergic receptor mRNA from SK-N-MC cells. The probe we used (p174) was derived from human genomic DNA and was designed to span the putative translation termination site/donor splice site (FIG. 9, A; see also FIG. 5). Referring to FIG. 9, the cRNA probe derived from p146 is complementary to sequence within the first exon of the human $\beta_3$ receptor and is fully protected by SK-N-MC mRNA. The cRNA probe derived from p174 is complementary to genomic DNA sequence that spans the putative first exon/intron junction (FIG. 9A). Although SK-N-MC D3 mRNA protects the full p174 cRNA probe (256 nt), most $\beta_3$ transcripts utilize the donor splice signal as indicated by the protected fragment of 194 nt. If the $\beta_3$ receptor gene is intronless, then SK-N-MC RNA should fully protect the complementary 256 nucleotide probe. However, if the 5' donor splicing signal contained in the human $\beta_3$ receptor pre-mRNA is utilized in the SK-N-MC cells, then cellular RNA should protect exactly 194 nucleotides of the probe. We found that both 256 and 194 nt of the probe was protected by SK-N-MC RNA (FIG. 9B). The ability of SK-N-MC RNA to protect 194 nt of the probe indicated that the splice signals in the human $\beta_3$ receptor primary transcript are used by SK-N-MC cells, and thus, the gene contains at least one intron. However, unlike the expression of the rat $\beta_3$ receptor gene in adipocytes, the efficiency of splicing was not complete, as indicated by the 256 nt fragment. Thus, about one-fourth of the total $\beta_3$ receptor mRNA failed to undergo splicing; and, as originally proposed (Emorine et al., 1989, ibid), the translation of the protein would be predicted to terminate at this point. Nevertheless, the great majority of the transcripts were spliced by these cells, and it seemed likely that the human $\beta_3$ receptor gene encoded additional amino acids.

To verify whether the spliced human $\beta_3$ mRNA encodes additional amino acids, the relevant region of the human $\beta_3$ receptor cDNA from SK-N-MC cells was cloned using RACE. Shown in FIG. 10 are the nucleic acid (SEQ. ID. NO. 3) and deduced amino acid (SEQ. ID. NO. 4) sequences of the human $\beta_3$ receptor cDNA we obtained. Shown in 10B is the human $\beta_3$ receptor cDNA (p184) (SEQ. ID. NO. 3) that was obtained from SK-N-MC cells using RACE, beginning with the codon for Ala$^{392}$ (FIG. 10A). The 5' cDNA sequence of the clone is identical to the published sequence of the human gene (Emorine et al., 1991, ibid) for 194 bp, then diverges (Bold) exactly at the predicted 5' donor site. The open reading frame continued for 6 amino acids, followed by 657 bp of nontranslated sequence. FIG. 10B shows the complete nucleic acid sequence of p184. (SEQ. ID. NO. 3) Shown in bold is sequence encoding the novel exon(s). Example 1 sets forth further details of the cloning of p184.

Figure 11:
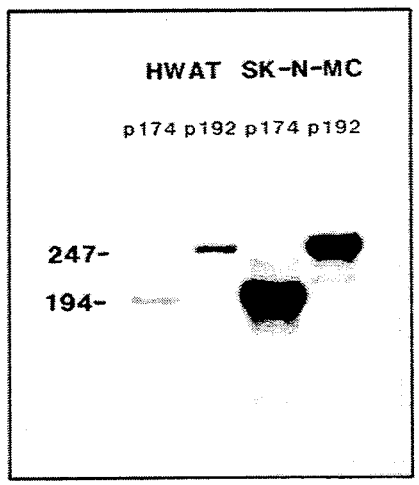
FIG. 11. Analysis of $\beta_3$-receptor RNA from human white adipose tissue and SK-N-MC cells.

We also verified that the cDNA sequence obtained from SK-N-MC cells was in fact expressed in normal human tissues (FIG. 11). Normal human adipose tissue expresses $\beta_3$ receptor mRNA containing two protein-coding exons. Details of this experiment are set forth in Example 5 hereof.

To further verify the GT donor splice site, RNA was obtained from CHO cells that had been transfected to express the truncated (encoding 402 amino acids) human $\beta_3$ receptor gene and was subjected to RNase protection analysis with a cRNA probe derived from the human $\beta_3$ receptor gene (p174, FIG. 9). CHO cellular RNA protected both 256 nt and 194 nt of the cRNA probe. The presence of the 194 nt fragment demonstrates that the 5' donor splice signal present in the gene is utilized by CHO cells, and results in the splicing of the first exon with sequences with the expression vector or at the site of DNA integration. Such splicing would be expected to produce a fusion protein, making cells that express such constructs unacceptable for drug screening.

Example 3 set forth below describes means for eliminating fusion proteins by site-directed mutagenesis. The purpose of the site-directed mutagenesis is to alter the codon for gly$^{402}$ so as to eliminate the donor splice signal in order to prevent production of fusion proteins. This modification is important because the splicing of the $\beta_3$ receptor premRNA is not complete and can potentially encode both a 402 amino acid receptor, as well as a fusion protein.

EXAMPLE 1

Cloning of a partial human $\beta_3$ receptor cDNA (p184). (SEQ. ID. NO. 3)

A partial human $\beta_3$ receptor cDNA was cloned by the rapid amplification of cDNA ends (RACE) technique (Frohman et al., 1990, ibid). General cloning techniques used are described in Maniatis et al., ibid. Total RNA (10 µg) from SK-N-MC cells was reverse-transcribed as described previously (Granneman, et al., 1991, Molecular Pharmacol. 40, 895-899) with a 17mer poly T deoxyoligonucleotide primer containing an engineered XbaI an BamHI restriction sites on the 5' end (5'ACTATAGGGTCTAGAG-GATCCGTTTTTTTTTTTTTTTTT 3'). The resulting cDNA was amplified with the human $\beta_3$ coding strand was 5' TGCGAATTCTGCCTT-CAACCCGCTC 3. The noncoding strand primer was 5' ACTATAGGGTCTAGAGGATCCG 3', which was the adapter sequence of the primer/adapter oligonucleotide described above. PCR was performed for 30 rounds as follows: Samples were denatured at 94° C. for 2 min., annealed at 58° C. for 2 min. and extended at 72° C. for 4 min. The resulting products digested with EcoRI and XbaI, then cloned into pGEM-7z. Twelve recombinants were screened to determine insert size. Analysis of two clones by RNase protection assay with the p174 cRNA probe indicated that the 870 bp inserts they contained encoded a human $\beta_3$ receptor cDNA. These clones were then analyzed by restriction mapping and dideoxynucleotide sequencing, and were found to be the same. The complete nucleotide sequence of p184 is given in FIG. 10. (SEQ. ID. NO. 3)

EXAMPLE 2

Gene construct Encoding Full-Length (408 a.a.) Human $\beta_3$-Adrenergic Receptor. (SEQ. ID. NO. 2)

(A) DNA

Figure 14:
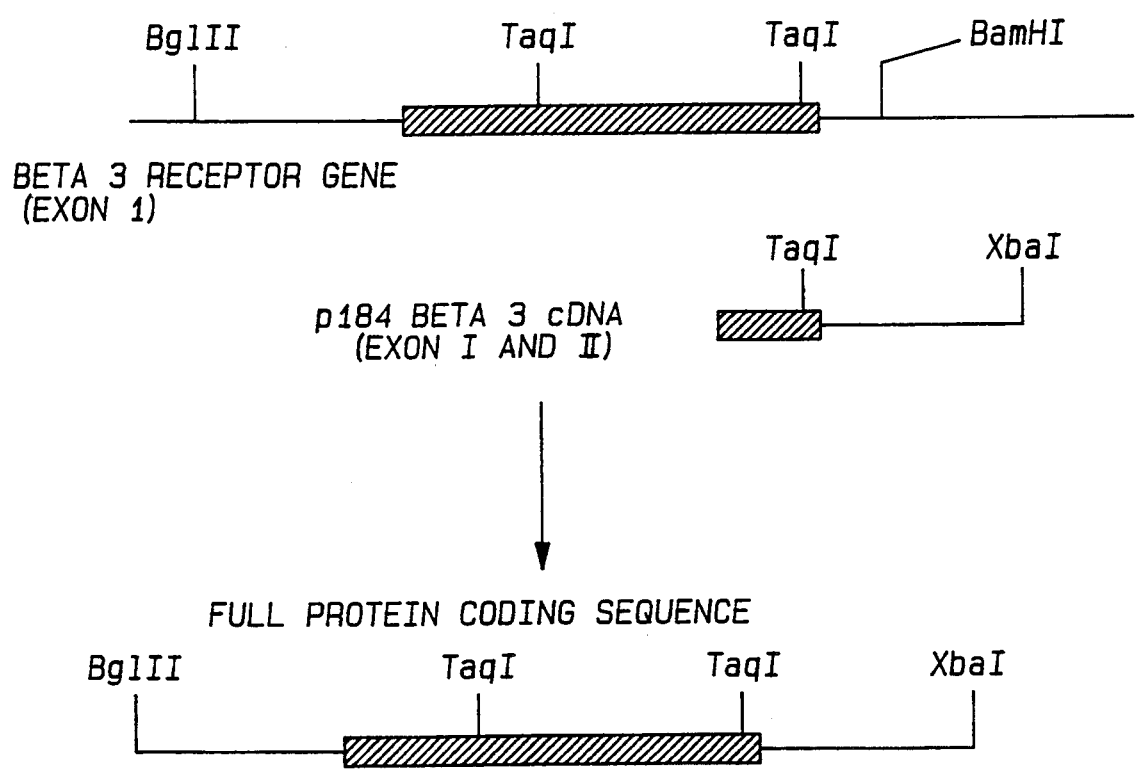
FIG. 14. Shows the construction of the full coding sequence for the human $\beta_3$ receptor.

Such constructs are made as follows: A human $\beta_3$ receptor genomic clone is obtained by screening a human genomic library (Clontech) with a radiolabelled probe derived from p184, described above in Example 1. The phage DNA is digested with BglII and BamHI and this 2 kb fragment cloned into pGEM-7z. This construct contains the first exon and part of the first intron of the human $\beta_3$ receptor gene. This construct is digested with TaqI (in exon 1) and XbaI (in the vector polylinker). The TaqI to XbaI fragment is removed and the two fragments, containing sequence from XbaI to TaqI (vector/5' gene) and sequence from TaqI to TaqI (in exon 1), is recovered. A three-way ligation is performed using the fragments just described and the TaqI to XbaI fragment of p184. The resulting construct contains an open reading frame that encodes the full-length human $\beta_3$ receptor. This construct and its preparation are depicted schematically in FIG. 14.

Alternatively, DNA encoding the full-length human $\beta_3$ receptor is also obtained by oligonucleotide-directed mutagenesis of truncated (402 amino acid) clones, using commercially-available kits (e.g. Amersham) DNA sequence encoding exon 1 and more than 25 bp of the first intron of the human beta 3 gene (Emorine et al., 1989, ibid) is cloned into a M-13 vector, or equivalent, single-stranded vector. Either the coding strand (FIG. 1) (SEQ. ID. NO. 1) or complementary strand may be used. The single-stranded DNA just described is hybridized to an oligonucleotide containing sequence that is complementary to the native genomic strand. The 5' end of the oligonucleotide is complementary to the end of exon 1 to the splice site (FIG. 10A). The next 19 nucleotides begin with G, followed by the codons for ala set trp gly val ser. The 3' end of the oligonucleotide continues with the sequence at the start of the first intron. For example: the oligonucleotide 5' CCAGGCTTTGCCAACGGCT-CGACGGGGCTTCTTGGGGAGTTTCTTAGG-TAACCGGGGCAGAGGGACC 3' (or its complement) is hybridized to the appropriate single stranded DNA. Useful variants of the oligonucleotide include those that are somewhat longer or shorter on the 5' or 3' ends. The oligonucleotide is extended with Klenow polymerase using dCTPαS, and ligated. Single-stranded DNA is removed, and the native strand is then nicked with NciI and digested with exonuclease III. The DNA is repolymerized and ligated, then transformed into host cell (e.g. E. coli).

(B) Procaryotic and eucaryotic vectors containing DNA described in (A)

The DNA sequence encoding the 408 amino acid human $\beta_3$ receptor protein (SEQ. ID. NO. 2) is first cloned into an appropriate commercially available vector for propagation of bacteria. In the present example, the insert described above is cloned into pGEM-7z. The protein-coding insert is then shuttled into appropriate mammalian expression vectors. In this case, we use pRc/CMV (Invitrogen), an expression vector containing the cytomegalovirus promoter and neomycin resistance gene. In the case of pRc/CMV, we take advantage of the HindIII and XbaI sites in the vector to shuttle the insert from pGEM-7z.

(C) Host cells that have been transfected to express the proteins encoded by the DNA constructs described in (B).

(1) Procaryotic cells used to propagate the plasmids are various strains of *E. coli*, including JM109, HB101 and DH5α. These cells are transformed using standard techniques known to the art.

(2) Eucaryotic cells

Chinese hamster ovary (CHO) cells are transfected with constructs based upon the expression vector pRc/CMV. CHO cells are preferred because they do not natively express any known β receptor subtype. Transfection of CHO cells with DNA constructs is accomplished by the $CaPO_4$-DNA precipitation method as described in Maniatis et al., ibid. To obtain cells that stably express these DNA constructs, transfected cells are selected based upon their resistance to G418, which is conferred by the neomycin-resistance gene contained in pRc/CMV. Cells that survive selective conditions (e.g. 800 μg/ml G418) are then cloned by limiting dilution. The stable expression of the human $β_3$ receptor is verified by (a) the presence of human $β_3$, receptor mRNA, determined by nuclease protection assay (see below), and (b) by the stimulation of adenylyl cyclase (e.g., Granneman et al. ibid) with selective $β_3$ receptor agonists such as BRL 37344 (1 μM), as well as the stimulation by isoproterenol (10 μM) that is resistant to blockade by CGP 20712A (100 nM).

EXAMPLE 3

Construct encoding alternative (402a.a.) human $β_3$ receptor wherein $Gly^{402}$ is degenerate.

DNA constructs encoding the first exon of the human $β_3$ receptor in which the codon for $glycine^{402}$ is made degenerate to alter the sequence GGGTAG so as to eliminate the donor splice signal is prepared by site-directed mutagenesis is performed using a commercially available kit (Amersham) as described in Example 2, except that the oligonucleotide is 5' CCAGGCTTTG-CCAACGGCTCGACGG(T/C/A)TAGG-TAACCGGGGCAGA GGGACC 3'. Following this procedure the sequence GGGTAG will be changed to GGTTAG, GGCTAG, and GGATAG, respectively.

EXAMPLE 4

A method for using the cells described in Example 2C to screen agents that specifically interact (either as agonists or antagonists) with the protein product of such DNA sequences.

CHO cells expressing the full length human $β_3$ receptor are harvested and membranes prepared as described by Granneman et al., ibid. Adenylyl cyclase activity is then determined in response to various agents known or thought to interact with the $β_3$ receptor, using the method of Salomon, ibid. Agonists are identified by the ability to increase cyclic AMP generation above basal levels. Antagonists are identified by their ability to decrease adenylyl cyclase activity that is stimulated by 100 nM isoproterenol.

The $β_3$ receptor is known to increase the formation of cyclic AMP; thus, the interaction of compounds with the recombinant proteins are monitored by changes in cyclic AMP (in whole cells or in cell membranes), or by monitoring the consequences of cyclic AMP formation. There are numerous ways to monitor cyclic AMP, including RIA and fluorescence immunoassay. In addition, the $β_3$ receptor may activate non-cyclic AMP responses, e.g. calcium influx. Therefore, there are several functional responses that are the consequence of the activation of these receptors.

Most preferably, these cells will be used to screen compounds that have potential antiobesity, antidiabetes and antispasmodic actions. These cells may also be of benefit in the screening of agents that alter body composition (e.g. repartitioning agents) of meat-producing animals.

EXAMPLE 5 p192 and a method of its use in the detection of human $β_3$ mRNA.

p184 (see FIGS. 10 and 14) contains sequences (SEQ. ID. NO. 3) that are useful in the analysis and detection of mRNA encoding the human $β_3$ receptor. To obtain one such sequence (p192) the EcoRI to NcoI fragment of p184 was cloned into pGEM-7z. The insert of p192 contains the first 292 bp of p184 and spans exon 1 and exon 2. This construct is used to generate cRNA probes for specific detection of human $β_3$ receptor mRNA or cDNA, using standard techniques. Shown in FIG. 11 is the use of p192 to detect human $β_3$ receptor cDNA that had been amplified with PCR. This was performed as follows: RNA from human adipose tissue and SK-N-MC cells was reverse transcribed with an oligonucleotide primer (5'CAACA-GAGTTGTTGCTTCTTGTCC 3') that was based upon exon 2 of the cDNA derived from SK-N-MC cells. The resulting cDNA amplified by PCR with this primer and primer HB3G+ (see methods). PCR products were then identified by nuclease protection assay with gene- (p174 - FIG. 9) and cDNA-derived (p192) probes (FIG. 11). The fact that human adipose tissue cDNA protects exactly 247 nt of the p192 probe and 194 nt of the p174 probe demonstrate that mRNA corresponding to the novel $β_3$ receptor cDNA we have cloned from SK-N-MC cells (SEQ. ID. NO. 1) is expressed in normal human adipose tissue (see FIG. 11).

Figure 12:
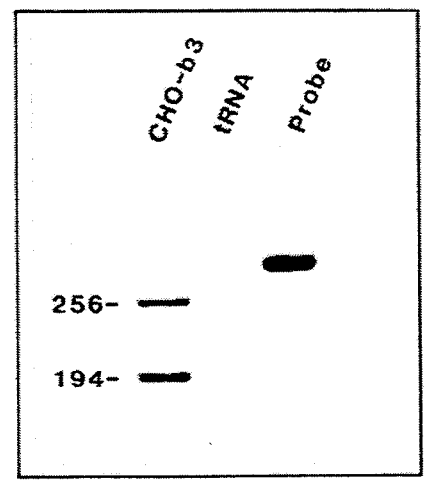
FIG. 12. CHO cells expressing the truncated human $\beta_3$ receptor gene make mRNA encoding an unanticipated fusion protein.

A number of sequences in p184 (SEQ. ID. NO. 3) are useful for diagnosis. These include the PCR primers described above. In general, all sequences that hybridize to either strand of p184 are useful. Most preferably, these are sequences (like p192) that can be used to distinguish $β_3$ receptor mRNA from genomic DNA by DNA amplification techniques (e.g. polymerase chain reaction, for example see FIG. 11) or that can be used to identify or quantify human $β_3$ receptor mRNA or mRNA splice variants (e.g. ribonuclease protection assay or RNA hybridization blot analysis (for example FIG. 12). Such sequences are useful in monitoring $β_3$ receptor gene expression for diagnosis or for development of agents that alter $β_3$ receptor expression.

EXAMPLE 6

Antibodies that are directed against the amino acid sequence: alanine serine tryptophan glycine valine serine.

Polyclonal and monoclonal antibodies are generated against the synthetic peptide by conventional techniques using commercially available services (Chiron, Emeryville, Calif.). To determine levels of expression of the $β_3$ receptor, antibodies may be useful in diagnosis to determine levels of expression of the $β_3$ receptor.

EXAMPLE 7

DNA constructs containing sequences within the introns or 5' flanking regions of the rat $β_3$ receptor gene (see FIG. 2C).

The rat $\beta_3$ receptor gene is expressed in a fat-specific fashion (Granneman et al., Molecular Pharmacol., 3991, 40, 895–899). Thus, the gene contains elements that confer fat-specific expression. To obtain the rat $\beta_3$ receptor gene, including the elements that control its expression in fat cells, we screened a rat cDNA library with a rat $\beta_3$ cDNA clone. DNA fragments of the gene and cDNA were cloned so as to obtain the DNA sequence of the entire rat gene. The location of the clones obtained are given in FIG. 2, p111 is a 3 kb XhoI to SmaI fragment containing the rat $\beta_3$ receptor 5' flanking promoter region, p108 contains the internal 211 bp SmaI to XhoI fragment and p167 contains the 2.6 kb XhoI to SphI fragment, which includes the first and second introns and the second and third exons. Sequence analysis of the first intron of the rat $\beta_3$ receptor gene indicates it contains elements involved in fat-specific gene expression.

EXAMPLE 8

Reporter gene constructs that contain elements described in Example 7, that are designed to modify the cellular transcription of the reporter gene.

Figure 13:
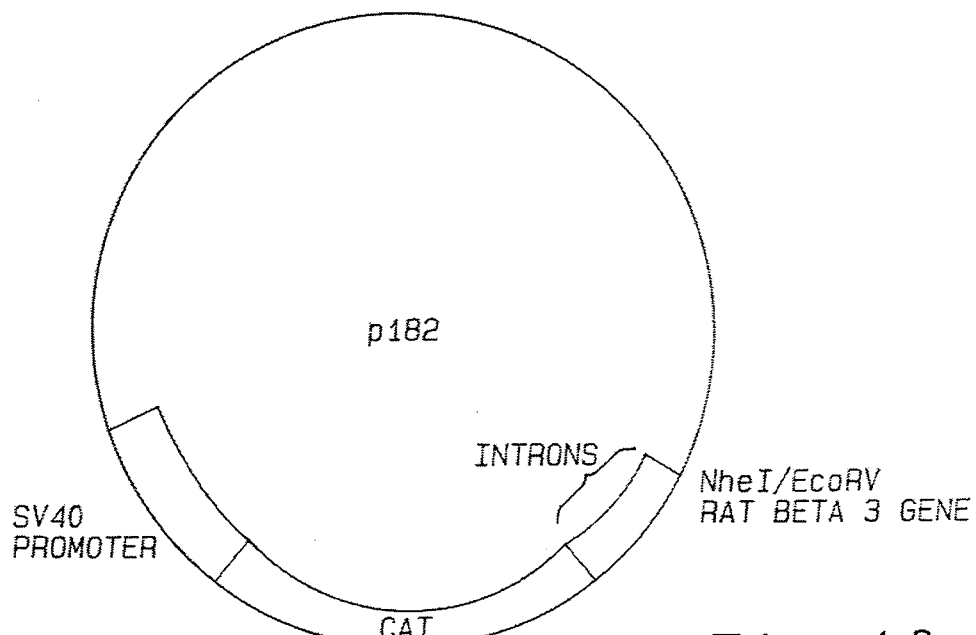
FIG. 13. Shows a reporter gene construct that expresses rat fat-specific elements.

The following construct (p182) has been made: The NheI to EcoRV fragment of p167, containing the first and second introns of the rat $\beta_3$ receptor gene (see 7 above), was cloned into pCAT promoter vector (Promega, Madison Wis.). This construct contains the SV40 promoter, and the introns have been cloned in such a way as to modify the activity of the promoter (FIG. 13). Although we used the chloramphenicol acetyltransferase reporter, there are numerous reporter genes that can be used, e.g. beta galactosidase, luciferase, inter alia). Alternatively, fat-specific elements, especially those in the 5' flanking region contained in p111 could be used in the construct.

EXAMPLE 9

Mammalian cells expressing p182.

3T3-F442A cells are stably transfected with constructs described in Example 8 by co-transfecting with pRC/CMV and selection with G418. Stable tranformants are identified by increase in reporter gene activity with insulin, and a decrease in reporter gene activity with tumor necrosis factor $\alpha$.

Other appropriate cells into which the construct could be transfected include those that express fat-specific transcription factors or demonstrate the ability to differentiate into an adipocyte phenotype in vitro. Examples of such cells are 3T3-F442A cells, 3T3-L1 cells and RMT preadipose cells. Included are the non-differentiated phenotypes of these cells.

Either transient or stable transfections can be used. These can be accomplished by numerous techniques, including CaPO$_4$, and liposome-mediated transfer (Transfectam, Promega, Madison, Wis.) and electroporation. The activity of the reporter gene is monitored by commercially-available kits (e.g. Promega, Madison, Wis.).

EXAMPLE 10

A method for using cells described in Example 9 to screen agents for gene-modulating activity.

3T3-F442A cells that have been stably transfected with a $\beta_3$ promoter/$\beta$-galactosidase reporter gene construct (p182) are plated in 96-well format. Preadipocytes and differentiated adipocytes are treated with the compound of interest. The activity of the reporter gene will be monitored by the fluorescent product of the Imagene (Molecular probes) $\beta$ galactosidase substrate with a Cytofluor fluorescence plate reader.

The use of the rat $\beta_3$ promoter is not limited to in vitro analysis. The genetic elements controlling fat-specific expression can be used to target the expression of transgenes to adipocytes of transgenic animals.

EXAMPLE 11

Isolation of the introns within the human and murine $\beta_3$ receptor gene.

Our discovery of an additional exon in the human and murine $\beta_3$ receptor genes allows for the cloning and elucidation of the correct genetic structure of the human and murine $\beta_3$ receptor genes. The genetic sequences that intervene the exons in the human gene are obtained by screening a commercially available human genomic library (Clontech) with a radiolabelled BamHI to XbaI fragment of p184 (FIG. 10B). (SEQ. ID. NO. 3) The resulting clone is digested with BamHI, and the bands that hybridize to the full EcoRI to XbaI insert of p184 are gel-isolated and cloned into BamHI linearized, phosphatase-treated pGEM-7z. To obtain the sequences that intervene the novel mouse exons, a commercially-available mouse genomic library (Clontech) is screened with a radiolabelled probe derived from p158, which encodes the novel mouse exons (SEQ. ID. NO. 8) described above.

Alternative methods include PCR using oligonucleotides that hybridize to p184 or p158.

We claim:

1. An isolated and purified DNA molecule which encodes a mammalian $\beta_3$-adrenergic receptor, selected from the group consisting of the coding sequence for human (SEQ. ID. NO. 1), and the coding sequence for mouse (SEQ. ID. NO. 8).

2. A nucleic acid molecule of claim 1 which is cDNA.

3. A nucleic acid molecule of claim 1 which is mRNA or cRNA.

4. A vector which comprises the DNA of claim 1.

5. A host cell transformed with the vector of claim 4.

6. A host cell of claim 5 which does not express other $\beta$ adrenergic receptors.

7. A method of preparing a $\beta_3$-adrenergic receptor which comprises culturing a host cell of claim 6 and isolating cell membranes containing the $\beta_3$-adrenergic receptor.

8. A vector of claim 4 which is a shuttle vector.

9. A host cell which is transformed with the vector of claim 8.

10. A host cell of claim 9 which does not express other $\beta$-adrenergic receptors 11. A method of preparing a $\beta_3$-adrenergic receptor which comprises culturing a host cell of claim 10 and isolating cell membranes containing the $\beta_3$-adrenergic receptor.

12. A purified and isolated DNA molecule which encodes the first exon of $\beta_3$-adrenergic receptor consisting of the coding sequence for human (SEQ. ID. NO. 1), wherein the nucleotide at position 1206 is changed from guanine (G) to a nucleotide selected from thymine (T), adenine (A) or cytosine (C).

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1227 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..1224

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GCT | CCG | TGG | CCT | CAC | GAG | AAC | AGC | TCT | CTT | GCC | CCA | TGG | CCG | GAC | 48 |
| Met | Ala | Pro | Trp | Pro | His | Glu | Asn | Ser | Ser | Leu | Ala | Pro | Trp | Pro | Asp | |
| 1 | | | | 5 | | | | | 10 | | | | | 15 | | |
| CTC | CCC | ACC | CTG | GCG | CCC | AAT | ACC | GCC | AAC | ACC | AGT | GGG | CTG | CCA | GGG | 96 |
| Leu | Pro | Thr | Leu | Ala | Pro | Asn | Thr | Ala | Asn | Thr | Ser | Gly | Leu | Pro | Gly | |
| | | | 20 | | | | | 25 | | | | | 30 | | | |
| GTT | CCG | TGG | GAG | GCG | GCC | CTA | GCC | GGG | GCC | CTG | CTG | GCG | CTG | GCG | GTG | 144 |
| Val | Pro | Trp | Glu | Ala | Ala | Leu | Ala | Gly | Ala | Leu | Leu | Ala | Leu | Ala | Val | |
| | | | 35 | | | | 40 | | | | | 45 | | | | |
| CTG | GCC | ACC | GTG | GGA | GGC | AAC | CTG | CTG | GTC | ATC | GTG | GCC | ATC | GCC | TGG | 192 |
| Leu | Ala | Thr | Val | Gly | Gly | Asn | Leu | Leu | Val | Ile | Val | Ala | Ile | Ala | Trp | |
| | 50 | | | | | 55 | | | | | 60 | | | | | |
| ACT | CCG | AGA | CTC | CAG | ACC | ATG | ACC | AAC | GTG | TTC | GTG | ACT | TCG | CTG | GCC | 240 |
| Thr | Pro | Arg | Leu | Gln | Thr | Met | Thr | Asn | Val | Phe | Val | Thr | Ser | Leu | Ala | |
| 65 | | | | | 70 | | | | | 75 | | | | | 80 | |
| GCA | GCC | GAC | CTG | GTG | ATG | GGA | CTC | CTG | GTG | GTG | CCG | CCG | GCG | GCC | ACC | 288 |
| Ala | Ala | Asp | Leu | Val | Met | Gly | Leu | Leu | Val | Val | Pro | Pro | Ala | Ala | Thr | |
| | | | | 85 | | | | | 90 | | | | | 95 | | |
| TTG | GCG | CTG | ACT | GGC | CAC | TGG | CCG | TTG | GGC | GCC | ACT | GGC | TGC | GAG | CTG | 336 |
| Leu | Ala | Leu | Thr | Gly | His | Trp | Pro | Leu | Gly | Ala | Thr | Gly | Cys | Glu | Leu | |
| | | | 100 | | | | | 105 | | | | | 110 | | | |
| TGG | ACC | TCG | GTG | GAC | GTG | CTG | TGT | GTG | ACC | GCC | AGC | ATC | GAA | ACC | CTG | 384 |
| Trp | Thr | Ser | Val | Asp | Val | Leu | Cys | Val | Thr | Ala | Ser | Ile | Glu | Thr | Leu | |
| | | 115 | | | | | 120 | | | | | 125 | | | | |
| TGC | GCC | CTG | GCC | GTG | GAC | CGC | TAC | CTG | GCT | GTG | ACC | AAC | CCG | CTG | CGT | 432 |
| Cys | Ala | Leu | Ala | Val | Asp | Arg | Tyr | Leu | Ala | Val | Thr | Asn | Pro | Leu | Arg | |
| | 130 | | | | | 135 | | | | | 140 | | | | | |
| TAC | GGC | GCA | CTG | GTC | ACC | AAG | CGC | TGC | GCC | CGG | ACA | GCT | GTG | GTC | CTG | 480 |
| Tyr | Gly | Ala | Leu | Val | Thr | Lys | Arg | Cys | Ala | Arg | Thr | Ala | Val | Val | Leu | |
| 145 | | | | | 150 | | | | | 155 | | | | | 160 | |
| GTG | TGG | GTC | GTG | TCG | GCC | GCG | GTG | TCG | TTT | GCG | CCC | ATC | ATG | AGC | CAG | 528 |
| Val | Trp | Val | Val | Ser | Ala | Ala | Val | Ser | Phe | Ala | Pro | Ile | Met | Ser | Gln | |
| | | | | 165 | | | | | 170 | | | | | 175 | | |
| TGG | TGG | CGC | GTA | GGG | GCC | GAC | GCC | GAG | GCG | CAG | CGC | TGC | CAC | TCC | AAC | 576 |
| Trp | Trp | Arg | Val | Gly | Ala | Asp | Ala | Glu | Ala | Gln | Arg | Cys | His | Ser | Asn | |
| | | | 180 | | | | | 185 | | | | | 190 | | | |
| CCG | CGC | TGC | TGT | GCC | TTC | GCC | TCC | AAC | ATG | CCC | TAC | GTG | CTG | CTG | TCC | 624 |
| Pro | Arg | Cys | Cys | Ala | Phe | Ala | Ser | Asn | Met | Pro | Tyr | Val | Leu | Leu | Ser | |
| | | 195 | | | | | 200 | | | | | 205 | | | | |
| TCC | TCC | GTC | TCC | TTC | TAC | CTT | CCT | CTT | CTC | GTG | ATG | CTC | TTC | GTC | TAC | 672 |
| Ser | Ser | Val | Ser | Phe | Tyr | Leu | Pro | Leu | Leu | Val | Met | Leu | Phe | Val | Tyr | |
| | 210 | | | | | 215 | | | | | 220 | | | | | |
| GCG | CGG | GTT | TTC | GTG | GTG | GCT | ACG | CGC | CAG | CTG | CGC | TTG | CTG | CGC | GGG | 720 |
| Ala | Arg | Val | Phe | Val | Val | Ala | Thr | Arg | Gln | Leu | Arg | Leu | Leu | Arg | Gly | |
| 225 | | | | | 230 | | | | | 235 | | | | | 240 | |
| GAG | CTG | GGC | CGC | TTT | CCG | CCC | GAG | GAG | TCT | CCG | CCG | GCG | CCG | TCG | CGC | 768 |
| Glu | Leu | Gly | Arg | Phe | Pro | Pro | Glu | Glu | Ser | Pro | Pro | Ala | Pro | Ser | Arg | |
| | | | | 245 | | | | | 250 | | | | | 255 | | |
| TCT | CTG | GCC | CCG | GCC | CCG | GTG | GGG | ACG | TGC | GCT | CCG | CCC | GAA | GGG | GTG | 816 |
| Ser | Leu | Ala | Pro | Ala | Pro | Val | Gly | Thr | Cys | Ala | Pro | Pro | Glu | Gly | Val | |
| | | | 260 | | | | | 265 | | | | | 270 | | | |
| CCC | GCC | TGC | GGC | CGG | CGG | CCC | GCG | CGC | CTC | CTG | CCT | CTC | CGG | GAA | CAC | 864 |
| Pro | Ala | Cys | Gly | Arg | Arg | Pro | Ala | Arg | Leu | Leu | Pro | Leu | Arg | Glu | His | |
| | | 275 | | | | | 280 | | | | | 285 | | | | |
| CGG | GCC | CTG | TGC | ACC | TTG | GGT | CTC | ATC | ATG | GGC | ACC | TTC | ACT | CTC | TGC | 912 |
| Arg | Ala | Leu | Cys | Thr | Leu | Gly | Leu | Ile | Met | Gly | Thr | Phe | Thr | Leu | Cys | |
| | 290 | | | | | 295 | | | | | 300 | | | | | |
| TGG | TTG | CCC | TTC | TTT | CTG | GCC | AAC | GTG | CTG | CGC | GCC | CTG | GGG | GGC | CCC | 960 |
| Trp | Leu | Pro | Phe | Phe | Leu | Ala | Asn | Val | Leu | Arg | Ala | Leu | Gly | Gly | Pro | |
| 305 | | | | | 310 | | | | | 315 | | | | | 320 | |

```
TCT  CTA  GTC  CCG  GGC  CCG  GCT  TTC  CTT  GCC  CTG  AAC  TGG  CTA  GGT  TAT        1008
Ser  Leu  Val  Pro  Gly  Pro  Ala  Phe  Leu  Ala  Leu  Asn  Trp  Leu  Gly  Tyr
                         325                 330                      335

GCC  AAT  TCT  GCC  TTC  AAC  CCG  CTC  ATC  TAC  TGC  CGC  AGC  CCG  GAC  TTT        1056
Ala  Asn  Ser  Ala  Phe  Asn  Pro  Leu  Ile  Tyr  Cys  Arg  Ser  Pro  Asp  Phe
               340                      345                     350

CGC  AGC  GCC  TTC  CGC  CGT  CTT  CTG  TGC  CGC  TGC  GGC  CGT  CGC  CTG  CCT        1104
Arg  Ser  Ala  Phe  Arg  Arg  Leu  Leu  Cys  Arg  Cys  Gly  Arg  Arg  Leu  Pro
          355                      360                     365

CCG  GAG  CCC  TGC  GCC  GCC  GCC  CGC  CCG  GCC  CTC  TTC  CCC  TCG  GGC  GTT        1152
Pro  Glu  Pro  Cys  Ala  Ala  Ala  Arg  Pro  Ala  Leu  Phe  Pro  Ser  Gly  Val
     370                      375                     380

CCT  GCG  GCC  CGG  AGC  AGC  CCA  GCG  CAG  CCC  AGG  CTT  TGC  CAA  CGG  CTC        1200
Pro  Ala  Ala  Arg  Ser  Ser  Pro  Ala  Gln  Pro  Arg  Leu  Cys  Gln  Arg  Leu
385                      390                     395                      400

GAC  GGG  GCT  TCT  TGG  GGA  GTT  TCT  TAG                                           1227
Asp  Gly  Ala  Ser  Trp  Gly  Val  Ser
                    405
```

(2) INFORMATION FOR SEQ ID NO:2:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Ala  Pro  Trp  Pro  His  Glu  Asn  Ser  Ser  Leu  Ala  Pro  Trp  Pro  Asp
 1                    5                        10                      15

Leu  Pro  Thr  Leu  Ala  Pro  Asn  Thr  Ala  Asn  Thr  Ser  Gly  Leu  Pro  Gly
               20                       25                      30

Val  Pro  Trp  Glu  Ala  Ala  Leu  Ala  Gly  Ala  Leu  Leu  Ala  Leu  Ala  Val
          35                      40                      45

Leu  Ala  Thr  Val  Gly  Gly  Asn  Leu  Leu  Val  Ile  Val  Ala  Ile  Ala  Trp
     50                      55                      60

Thr  Pro  Arg  Leu  Gln  Thr  Met  Thr  Asn  Val  Phe  Val  Thr  Ser  Leu  Ala
65                       70                      75                       80

Ala  Ala  Asp  Leu  Val  Met  Gly  Leu  Leu  Val  Val  Pro  Pro  Ala  Ala  Thr
               85                      90                       95

Leu  Ala  Leu  Thr  Gly  His  Trp  Pro  Leu  Gly  Ala  Thr  Gly  Cys  Glu  Leu
               100                     105                     110

Trp  Thr  Ser  Val  Asp  Val  Leu  Cys  Val  Thr  Ala  Ser  Ile  Glu  Thr  Leu
          115                     120                     125

Cys  Ala  Leu  Ala  Val  Asp  Arg  Tyr  Leu  Ala  Val  Thr  Asn  Pro  Leu  Arg
     130                     135                     140

Tyr  Gly  Ala  Leu  Val  Thr  Lys  Arg  Cys  Ala  Arg  Thr  Ala  Val  Val  Leu
145                      150                     155                      160

Val  Trp  Val  Val  Ser  Ala  Ala  Val  Ser  Phe  Ala  Pro  Ile  Met  Ser  Gln
               165                     170                     175

Trp  Trp  Arg  Val  Gly  Ala  Asp  Ala  Glu  Ala  Gln  Arg  Cys  His  Ser  Asn
               180                     185                     190

Pro  Arg  Cys  Cys  Ala  Phe  Ala  Ser  Asn  Met  Pro  Tyr  Val  Leu  Leu  Ser
          195                     200                     205

Ser  Ser  Val  Ser  Phe  Tyr  Leu  Pro  Leu  Leu  Val  Met  Leu  Phe  Val  Tyr
     210                     215                     220

Ala  Arg  Val  Phe  Val  Val  Ala  Thr  Arg  Gln  Leu  Arg  Leu  Leu  Arg  Gly
225                      230                     235                      240
```

| | | | | | | | | | | | | | |
|---|---|---|---|---|---|---|---|---|---|---|---|---|---|
| Glu | Leu | Gly | Arg | Phe 245 | Pro | Pro | Glu | Glu | Ser 250 | Pro | Pro | Ala | Pro | Ser 255 | Arg |
| Ser | Leu | Ala | Pro 260 | Ala | Pro | Val | Gly | Thr 265 | Cys | Ala | Pro | Pro | Glu 270 | Gly | Val |
| Pro | Ala | Cys 275 | Gly | Arg | Arg | Pro | Ala 280 | Arg | Leu | Leu | Pro | Leu 285 | Arg | Glu | His |
| Arg | Ala 290 | Leu | Cys | Thr | Leu | Gly 295 | Leu | Ile | Met | Gly | Thr 300 | Phe | Thr | Leu | Cys |
| Trp 305 | Leu | Pro | Phe | Phe | Leu 310 | Ala | Asn | Val | Leu | Arg 315 | Ala | Leu | Gly | Gly | Pro 320 |
| Ser | Leu | Val | Pro | Gly 325 | Pro | Ala | Phe | Leu | Ala 330 | Leu | Asn | Trp | Leu | Gly 335 | Tyr |
| Ala | Asn | Ser | Ala 340 | Phe | Asn | Pro | Leu | Ile 345 | Tyr | Cys | Arg | Ser | Pro 350 | Asp | Phe |
| Arg | Ser | Ala 355 | Phe | Arg | Arg | Leu | Leu 360 | Cys | Arg | Cys | Gly | Arg 365 | Arg | Leu | Pro |
| Pro | Glu 370 | Pro | Cys | Ala | Ala | Ala 375 | Arg | Pro | Ala | Leu | Phe 380 | Pro | Ser | Gly | Val |
| Pro 385 | Ala | Ala | Arg | Ser | Ser 390 | Pro | Ala | Gln | Pro | Arg 395 | Leu | Cys | Gln | Arg | Leu 400 |
| Asp | Gly | Ala | Ser | Trp 405 | Gly | Val | Ser | | | | | | | | |

( 2 ) INFORMATION FOR SEQ ID NO:3:

( i ) SEQUENCE CHARACTERISTICS:
        ( A ) LENGTH: 870 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: exon
        ( B ) LOCATION: 1..195

( i x ) FEATURE:
        ( A ) NAME/KEY: exon
        ( B ) LOCATION: 196..870

( i x ) FEATURE:
        ( A ) NAME/KEY: CDS
        ( B ) LOCATION: 1..215

( x i ) SEQUENCE DESCRIPTION: SEQ ID NO:3:

```
AAT TCT GCC TTC AAC CCG CTC ATC TAC TGC CGC AGC CCG GAC TTT CGC       48
Asn Ser Ala Phe Asn Pro Leu Ile Tyr Cys Arg Ser Pro Asp Phe Arg
 1               5                  10                  15

AGC GCC TTC CGC CGT CTT CTG TGC CGC TGC GGC CGT CGC CTG CCT CCG       96
Ser Ala Phe Arg Arg Leu Leu Cys Arg Cys Gly Arg Arg Leu Pro Pro
            20                  25                  30

GAG CCC TGC GCC GCC GCC CGC CCG GCC CTC TTC CCC TCG GGC GTT CCT      144
Glu Pro Cys Ala Ala Ala Arg Pro Ala Leu Phe Pro Ser Gly Val Pro
        35                  40                  45

GCG GCC CGG AGC AGC CCA GCG CAG CCC AGG CTT TGC CAA CGG CTC GAC      192
Ala Ala Arg Ser Ser Pro Ala Gln Pro Arg Leu Cys Gln Arg Leu Asp
    50                  55                  60

GGG GCT TCT TGG GGA GTT TCT TA GGCCTGAAGG ACAAGAAGCA ACAACTCTGT      245
Gly Ala Ser Trp Gly Val Ser
65                  70

TGATCAGAAC CTGTGGAAAA CCTCTGGCCT CTGTTCAGAA TGAGTCCCAT GGGATTCCCC      305

GGCTGTGACA CTCTACCCTC CAGAACCTGA CGACTGGGCC ATGTGACCCA AGGAGGGATC      365
```

| | | | | |
|---|---|---|---|---|
| CTTACCAAGT | GGGTTTTCAC | CATCCTCTTG | CTCTCTGTCT | GAGAGATGTT TTCTAAACCC | 425 |
| CAGCCTTGAA | CTTCACTCCT | CCCTCAGTGG | TAGTGTCCAG | GTGCCGTGGA GCAGCAGGCT | 485 |
| GGCTTTGGTA | GGGGCACCCA | TCACCCGGCT | TGCCTGTGCA | GTCAGTGAGT GCTTAGGGCA | 545 |
| AAGAGAGCTC | CCCTGGTTCC | ATTCCTTCTG | CCACCCAAAC | CCTGATGAGA CCTTAGTGTT | 605 |
| CTCCAGGCTC | TGTGGCCCAG | GCTGAGAGCA | GCAGGGTAGA | AAAGACCAAG ATTTGGGGTT | 665 |
| TTATCTCTGG | TTCCCTTATT | ACTGCTCTCA | AGCAGTGGCC | TCTCTCACTT TAGCCATGGA | 725 |
| ATGGCTCCGA | TCTACCTCAC | AGCAGTGTCA | GAAGGACTTC | GCCAGGGTTT TGGGAGCTCC | 785 |
| AGGGTTCATA | AGAAGGTGAA | CCATTAGAAC | AGATCCCTTC | TTTTCCTTTT GCAATCAGAT | 845 |
| AAATAAATAT | CACTGAATGC | AGTTC | | | 870 |

(2) INFORMATION FOR SEQ ID NO:4:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:4:

```
Asn Ser Ala Phe Asn Pro Leu Ile Tyr Cys Arg Ser Pro Asp Phe Arg
 1               5                  10                  15

Ser Ala Phe Arg Arg Leu Leu Cys Arg Cys Gly Arg Arg Leu Pro Pro
                20                  25                  30

Glu Pro Cys Ala Ala Ala Arg Pro Ala Leu Phe Pro Ser Gly Val Pro
            35                  40                  45

Ala Ala Arg Ser Ser Pro Ala Gln Pro Arg Leu Cys Gln Arg Leu Asp
        50                  55                  60

Gly Ala Ser Trp Gly Val Ser
 65                  70
```

(2) INFORMATION FOR SEQ ID NO:5:

(i) SEQUENCE CHARACTERISTICS:
        (A) LENGTH: 2005 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: CDS
        (B) LOCATION: 51..1250

(xi) SEQUENCE DESCRIPTION: SEQ ID NO:5:

```
TAAGCCAGCG GGTCTGGGGG GAAAACTTCC CATCCCAGAC GCGACACGAG ATG GCT      56
                                                         Met Ala
                                                          1

CCG TGG CCT CAC AAA AAC GGC TCT CTG GCT TTC TGG TCA GAC GCC CCC    104
Pro Trp Pro His Lys Asn Gly Ser Leu Ala Phe Trp Ser Asp Ala Pro
         5                  10                  15

ACC TTG GAC CCC AGT GCA GCC AAC ACC AGT GGG TTG CCA GGG GTG CCA    152
Thr Leu Asp Pro Ser Ala Ala Asn Thr Ser Gly Leu Pro Gly Val Pro
         20                 25                  30

TGG GCA GCG GCA TTG GCT GGA GCA TTG CTG GCG CTG GCC ACG GTG GGA    200
Trp Ala Ala Ala Leu Ala Gly Ala Leu Leu Ala Leu Ala Thr Val Gly
 35                 40                  45                  50

GGC AAC CTG CTG GTA ATC ACA GCT ATC GCC CGC ACG CCG AGA CTA CAG    248
Gly Asn Leu Leu Val Ile Thr Ala Ile Ala Arg Thr Pro Arg Leu Gln
             55                 60                  65
```

| | | | | | | | | | | | | | | | | |
|---|---|---|---|---|---|---|---|---|---|---|---|---|---|---|---|---|
| ACC | ATA | ACC | AAC | GTG | TTC | GTG | ACT | TCG | CTG | GCC | ACA | GCT | GAC | TTG | GTA | 296 |
| Thr | Ile | Thr | Asn | Val | Phe | Val | Thr | Ser | Leu | Ala | Thr | Ala | Asp | Leu | Val | |
| | | | 70 | | | | | 75 | | | | | 80 | | | |
| GTG | GGA | CTC | CTC | GTA | ATG | CCA | CCA | GGG | GCC | ACA | TTG | GCG | CTG | ACT | GGC | 344 |
| Val | Gly | Leu | Leu | Val | Met | Pro | Pro | Gly | Ala | Thr | Leu | Ala | Leu | Thr | Gly | |
| | | 85 | | | | | 90 | | | | | 95 | | | | |
| CAC | TGG | CCC | TTG | GGC | GCA | ACT | GGC | TGC | GAG | CTG | TGG | ACG | TCA | GTG | GAC | 392 |
| His | Trp | Pro | Leu | Gly | Ala | Thr | Gly | Cys | Glu | Leu | Trp | Thr | Ser | Val | Asp | |
| | | 100 | | | | | 105 | | | | | 110 | | | | |
| GTG | CTC | TGT | GTA | ACT | GCC | AGC | ATC | GAG | ACC | CTG | TGC | GCC | CTG | GCT | GTA | 440 |
| Val | Leu | Cys | Val | Thr | Ala | Ser | Ile | Glu | Thr | Leu | Cys | Ala | Leu | Ala | Val | |
| 115 | | | | 120 | | | | | 125 | | | | | 130 | | |
| GAC | CGC | TAC | CTA | GCC | GTC | ACC | AAC | CCT | CTG | CGT | TAC | GGC | ACG | CTG | GTT | 488 |
| Asp | Arg | Tyr | Leu | Ala | Val | Thr | Asn | Pro | Leu | Arg | Tyr | Gly | Thr | Leu | Val | |
| | | | 135 | | | | | 140 | | | | | 145 | | | |
| ACC | AAG | CGC | CGC | GCC | CGG | GCG | GCA | GTA | GTC | CTG | GTG | TGG | ATC | GTG | TCC | 536 |
| Thr | Lys | Arg | Arg | Ala | Arg | Ala | Ala | Val | Val | Leu | Val | Trp | Ile | Val | Ser | |
| | | | 150 | | | | | 155 | | | | | 160 | | | |
| GCC | ACC | GTG | TCC | TTT | GCG | CCC | ATC | ATG | AGC | CAG | TGG | TGG | CGT | GTA | GGG | 584 |
| Ala | Thr | Val | Ser | Phe | Ala | Pro | Ile | Met | Ser | Gln | Trp | Trp | Arg | Val | Gly | |
| | | 165 | | | | | 170 | | | | | 175 | | | | |
| GCA | GAC | GCT | GAG | GCG | CAA | GAG | TGT | CAC | TCC | AAT | CCG | CGC | TGC | TGT | TCC | 632 |
| Ala | Asp | Ala | Glu | Ala | Gln | Glu | Cys | His | Ser | Asn | Pro | Arg | Cys | Cys | Ser | |
| | 180 | | | | | 185 | | | | | 190 | | | | | |
| TTT | GCC | TCC | AAT | ATG | CCC | TAC | GCG | CTG | CTC | TCC | TCC | TCC | GTC | TCC | TTC | 680 |
| Phe | Ala | Ser | Asn | Met | Pro | Tyr | Ala | Leu | Leu | Ser | Ser | Ser | Val | Ser | Phe | |
| 195 | | | | | 200 | | | | | 205 | | | | | 210 | |
| TAC | CTT | CCC | CTC | CTT | GTG | ATG | CTC | TTC | GTC | TAT | GCT | CGA | GTG | TTC | GTC | 728 |
| Tyr | Leu | Pro | Leu | Leu | Val | Met | Leu | Phe | Val | Tyr | Ala | Arg | Val | Phe | Val | |
| | | | | 215 | | | | | 220 | | | | | 225 | | |
| GTA | GCT | AAG | CGC | CAG | CGG | CGT | TTG | CTG | CGC | CGG | GAG | CTG | GGC | CGT | TTT | 776 |
| Val | Ala | Lys | Arg | Gln | Arg | Arg | Leu | Leu | Arg | Arg | Glu | Leu | Gly | Arg | Phe | |
| | | | 230 | | | | | 235 | | | | | 240 | | | |
| CCG | CCC | GAG | GAG | TCT | CCG | CGG | TCT | CCG | TCG | CGC | TCT | CCA | TCC | CCT | GCC | 824 |
| Pro | Pro | Glu | Glu | Ser | Pro | Arg | Ser | Pro | Ser | Arg | Ser | Pro | Ser | Pro | Ala | |
| | | 245 | | | | | 250 | | | | | 255 | | | | |
| ACA | GTC | GGG | ACA | CCC | ACG | GCA | TCG | GAT | GGA | GTG | CCC | TCC | TGC | GGG | CGG | 872 |
| Thr | Val | Gly | Thr | Pro | Thr | Ala | Ser | Asp | Gly | Val | Pro | Ser | Cys | Gly | Arg | |
| | 260 | | | | | 265 | | | | | 270 | | | | | |
| CGG | CCT | GCG | CGC | CTC | CTA | CCG | CTC | GGG | GAA | CAC | CGC | GCC | CTG | CGC | ACC | 920 |
| Arg | Pro | Ala | Arg | Leu | Leu | Pro | Leu | Gly | Glu | His | Arg | Ala | Leu | Arg | Thr | |
| 275 | | | | | 280 | | | | | 285 | | | | | 290 | |
| TTG | GGT | CTC | ATT | ATG | GGC | ATC | TTC | TCT | CTG | TGC | TGG | CTG | CCC | TTC | TTT | 968 |
| Leu | Gly | Leu | Ile | Met | Gly | Ile | Phe | Ser | Leu | Cys | Trp | Leu | Pro | Phe | Phe | |
| | | | | 295 | | | | | 300 | | | | | 305 | | |
| CTG | GCC | AAC | GTG | CTG | CGC | GCA | CTC | GTG | GGG | CCC | TCC | CTA | GTT | CCC | AGC | 1016 |
| Leu | Ala | Asn | Val | Leu | Arg | Ala | Leu | Val | Gly | Pro | Ser | Leu | Val | Pro | Ser | |
| | | | 310 | | | | | 315 | | | | | 320 | | | |
| GGA | GTT | TTC | ATC | GCC | CTG | AAC | TGG | TTG | GGC | TAT | GCC | AAC | TCT | GCC | TTC | 1064 |
| Gly | Val | Phe | Ile | Ala | Leu | Asn | Trp | Leu | Gly | Tyr | Ala | Asn | Ser | Ala | Phe | |
| | | 325 | | | | | 330 | | | | | 335 | | | | |
| AAC | CCG | CTC | ATC | TAC | TGC | CGC | AGC | CCG | GAC | TTT | CGC | GAC | GCC | TTC | CGT | 1112 |
| Asn | Pro | Leu | Ile | Tyr | Cys | Arg | Ser | Pro | Asp | Phe | Arg | Asp | Ala | Phe | Arg | |
| | 340 | | | | | 345 | | | | | 350 | | | | | |
| CGT | CTT | CTG | TGC | AGC | TAC | GGT | GGC | CGT | GGA | CCG | GAA | GAG | CCA | CGC | GTG | 1160 |
| Arg | Leu | Leu | Cys | Ser | Tyr | Gly | Gly | Arg | Gly | Pro | Glu | Glu | Pro | Arg | Val | |
| 355 | | | | | 360 | | | | | 365 | | | | | 370 | |
| GTC | ACC | TTC | CCA | GCT | AGC | CCT | GTT | GCG | TCC | AGG | CAG | AAC | TCA | CCG | CTC | 1208 |
| Val | Thr | Phe | Pro | Ala | Ser | Pro | Val | Ala | Ser | Arg | Gln | Asn | Ser | Pro | Leu | |
| | | | | 375 | | | | | 380 | | | | | 385 | | |
| AAC | AGG | TTT | GAT | GGC | TAT | GAA | GGT | GAG | CGT | CCA | TTT | CCC | ACA | | | 1250 |

| | | | | | | | | | | | |
|---|---|---|---|---|---|---|---|---|---|---|---|
|Asn|Arg|Phe|Asp|Gly|Tyr|Glu|Gly|Glu|Arg|Pro|Phe Pro Thr|
| | | |390| | | |395| | | |400|

```
TGAAGGACCA  TGGAGATCTA  GCAAGGAGCC  TGACTTCTGG  AGAAATTTTT  TTTTAAGACA   1310

GAAAGACAAG  CAACGTCCAT  GGATGCAAAC  CTTTTATCAG  CCCTTGATTC  TGCTCAGAGT   1370

GAGTTCCCAG  GAACCGCAAC  TCTCCAGACC  ATGCATAGAC  CACAGAATGT  AAAGGGGAAA   1430

TCTTACCAAA  TGGGTTTACC  ATCTTCTCTC  TCTTCGTGAG  AGTGTCTATA  GGCCACCTTG   1490

AACTTCGCTA  CTACCTCAGC  CGCCGGATAT  CAGCCACCCT  GCGTTGACTG  CCTGGGAGGA   1550

GCTGCGTTCC  CACCACCACC  CTGCTTATTA  TGTTTGTGCT  GGATGCTTAG  GGCTAAGAAA   1610

GCACCCTTAC  CTACCTCCCT  TCCTACGCTT  TCCTGACCCC  ATGAATGACT  TTTGTCTCCA   1670

CAAATCACTC  TGTCTCCAGG  TTCTGTGTTC  CCAGTCTCTG  TGTCTCTGGT  TAGTTGGAAA   1730

GCAGGAAACC  CGGCGGGGGA  GGCGGGGGAG  GGGGGGAACG  ACCAAGTTTG  AGGTTTTGTC   1790

CCTGGCTCCT  CACTACAGCT  CTCTAAACAT  CATCTTGGAC  CATCTCTCAC  AATAGGCACA   1850

AAACAGCTCT  AATCTACCTC  ACTCTTAGGA  CTTCAAGGTT  TGGGAGAAAT  TCCAGGGTTC   1910

CTGGGAAGAA  GTCAAACCAT  TGGAATGGGT  CCCTTTTGGC  GTTAAAATCA  AATTAATAAA   1970

TATTATTGAA  TGTGAAAAAA  AAAAAAAAAT  CTAGA                                2005
```

( 2 ) INFORMATION FOR SEQ ID NO:6:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ala  Pro  Trp  Pro  His  Lys  Asn  Gly  Ser  Leu  Ala  Phe  Trp  Ser  Asp
  1                  5                      10                      15

Ala  Pro  Thr  Leu  Asp  Pro  Ser  Ala  Ala  Asn  Thr  Ser  Gly  Leu  Pro  Gly
                20                      25                      30

Val  Pro  Trp  Ala  Ala  Ala  Leu  Ala  Gly  Ala  Leu  Leu  Ala  Leu  Ala  Thr
           35                      40                      45

Val  Gly  Gly  Asn  Leu  Leu  Val  Ile  Thr  Ala  Ile  Ala  Arg  Thr  Pro  Arg
     50                      55                      60

Leu  Gln  Thr  Ile  Thr  Asn  Val  Phe  Val  Thr  Ser  Leu  Ala  Thr  Ala  Asp
 65                      70                      75                      80

Leu  Val  Val  Gly  Leu  Leu  Val  Met  Pro  Pro  Gly  Ala  Thr  Leu  Ala  Leu
                85                      90                      95

Thr  Gly  His  Trp  Pro  Leu  Gly  Ala  Thr  Gly  Cys  Glu  Leu  Trp  Thr  Ser
           100                     105                     110

Val  Asp  Val  Leu  Cys  Val  Thr  Ala  Ser  Ile  Glu  Thr  Leu  Cys  Ala  Leu
          115                      120                     125

Ala  Val  Asp  Arg  Tyr  Leu  Ala  Val  Thr  Asn  Pro  Leu  Arg  Tyr  Gly  Thr
     130                     135                     140

Leu  Val  Thr  Lys  Arg  Arg  Ala  Arg  Ala  Ala  Val  Val  Leu  Val  Trp  Ile
145                      150                     155                      160

Val  Ser  Ala  Thr  Val  Ser  Phe  Ala  Pro  Ile  Met  Ser  Gln  Trp  Trp  Arg
                165                     170                     175

Val  Gly  Ala  Asp  Ala  Glu  Ala  Gln  Glu  Cys  His  Ser  Asn  Pro  Arg  Cys
           180                     185                     190

Cys  Ser  Phe  Ala  Ser  Asn  Met  Pro  Tyr  Ala  Leu  Leu  Ser  Ser  Ser  Val
     195                     200                     205

Ser  Phe  Tyr  Leu  Pro  Leu  Leu  Val  Met  Leu  Phe  Val  Tyr  Ala  Arg  Val
210                      215                     220
```

| | | | | | | | | | | | | | | |
|---|---|---|---|---|---|---|---|---|---|---|---|---|---|---|
| Phe | Val | Val | Ala | Lys | Arg | Gln | Arg | Arg | Leu | Leu | Arg | Arg | Glu | Leu | Gly |
| 225 | | | | 230 | | | | | 235 | | | | | 240 |
| Arg | Phe | Pro | Pro | Glu | Glu | Ser | Pro | Arg | Ser | Pro | Ser | Arg | Ser | Pro | Ser |
| | | | | 245 | | | | | 250 | | | | | 255 |
| Pro | Ala | Thr | Val | Gly | Thr | Pro | Thr | Ala | Ser | Asp | Gly | Val | Pro | Ser | Cys |
| | | | 260 | | | | | 265 | | | | | 270 | | |
| Gly | Arg | Arg | Pro | Ala | Arg | Leu | Leu | Pro | Leu | Gly | Glu | His | Arg | Ala | Leu |
| | | 275 | | | | | 280 | | | | | 285 | | | |
| Arg | Thr | Leu | Gly | Leu | Ile | Met | Gly | Ile | Phe | Ser | Leu | Cys | Trp | Leu | Pro |
| | 290 | | | | | 295 | | | | | 300 | | | | |
| Phe | Phe | Leu | Ala | Asn | Val | Leu | Arg | Ala | Leu | Val | Gly | Pro | Ser | Leu | Val |
| 305 | | | | | 310 | | | | | 315 | | | | | 320 |
| Pro | Ser | Gly | Val | Phe | Ile | Ala | Leu | Asn | Trp | Leu | Gly | Tyr | Ala | Asn | Ser |
| | | | | 325 | | | | | 330 | | | | | 335 | |
| Ala | Phe | Asn | Pro | Leu | Ile | Tyr | Cys | Arg | Ser | Pro | Asp | Phe | Arg | Asp | Ala |
| | | | 340 | | | | | 345 | | | | | 350 | | |
| Phe | Arg | Arg | Leu | Leu | Cys | Ser | Tyr | Gly | Gly | Arg | Gly | Pro | Glu | Glu | Pro |
| | | 355 | | | | | 360 | | | | | 365 | | | |
| Arg | Val | Val | Thr | Phe | Pro | Ala | Ser | Pro | Val | Ala | Ser | Arg | Gln | Asn | Ser |
| | 370 | | | | | 375 | | | | | 380 | | | | |
| Pro | Leu | Asn | Arg | Phe | Asp | Gly | Tyr | Glu | Gly | Glu | Arg | Pro | Phe | Pro | Thr |
| 385 | | | | | 390 | | | | | 395 | | | | | 400 |

( 2 ) INFORMATION FOR SEQ ID NO:7:

( i ) SEQUENCE CHARACTERISTICS:
        ( A ) LENGTH: 687 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 9..402

( i x ) FEATURE:
        ( A ) NAME/KEY: exon
        ( B ) LOCATION: 403..470

( i x ) FEATURE:
        ( A ) NAME/KEY: intron
        ( B ) LOCATION: 471..674

( x i ) SEQUENCE DESCRIPTION: SEQ ID NO:7:

| | | | | | | |
|---|---|---|---|---|---|---|
| CTCAACAGGT | AGGCGACGCA | GGCAGAGGAC | TGGAGTCTGG | GTGGGGACGC | CTCTGTCTCT | 60 |
| ATTTTTGAGT | TTGAGGGTTG | GGGGAGGAGA | AGGTGTAGAC | AGGGCTTTTG | TCTCGAGAGG | 120 |
| ACAGAAAAGG | AGTAAGAACA | GAATCGGGAT | CTAGGGCCCT | TCCTTTTATT | GGATCCAATC | 180 |
| CCTGGGTCTG | AGGCAAAGGA | GGAAAGGGAA | ATTTGTTCAC | CTTGGGACCA | GGTGAGCCCC | 240 |
| ACAGGTTTCT | GCCAGCAGGT | TTCTGACCTC | TCTGGTTGCC | TCTAGTTTGG | ATCTTTTTAG | 300 |
| TTCTATTCTC | CAGGCGCCCA | GGTATCACTA | ACTTGCTGG | GACATCCATA | GACAGCAATG | 360 |
| GACATGTCAA | GTCCTCTGCC | TCAGTTCCGC | TTTCTTTCAA | AGGTTTGATG | GCTATGAAGG | 420 |
| TGAGCGTCCA | TTTCCACAT | GAAGGACCAT | GGAGATCTAG | CAAGGAGCCT | GTGAGTTGAA | 480 |
| TTTGAGCTGC | TTTTCTCCCT | CAGGGACTGG | ATTCGAGGTG | TAGGGTGGGA | TGAGGGAGGG | 540 |
| TGCAGGATGA | TCCCTATATC | TTTGAAAAGT | AAATATGCTA | TTCAGGGTTC | CTGAGTCACT | 600 |
| CCCCTCTTAC | CTCCAGTGCT | TGATCCGCAC | CTCCTTGACT | GGTTACCCCA | AGAAATATTG | 660 |
| TTTCCGTTTT | GCAGGACTTC | TGGAGAA | | | | 687 |

( 2 ) INFORMATION FOR SEQ ID NO:8:

( i ) SEQUENCE CHARACTERISTICS:
        ( A ) LENGTH: 176 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: exon
        ( B ) LOCATION: 1..60

( i x ) FEATURE:
        ( A ) NAME/KEY: exon
        ( B ) LOCATION: 61..176

( i x ) FEATURE:
        ( A ) NAME/KEY: CDS
        ( B ) LOCATION: 2..97

( x i ) SEQUENCE DESCRIPTION: SEQ ID NO:8:

```
A CGC GCA GTC ACC TTC CCA GCC AGC CCT GTT GAA GCC AGG CAG AGT         46
  Arg Ala Val Thr Phe Pro Ala Ser Pro Val Glu Ala Arg Gln Ser
  1               5                  10                  15

CCA CCG CTC AAC AGG TTT GAT GGC TAT GAA GGT GCG CGT CCG TTT CCC       94
Pro Pro Leu Asn Arg Phe Asp Gly Tyr Glu Gly Ala Arg Pro Phe Pro
            20                  25                  30

ACG TGAAGGGCCG TGAAGATCCA GCAAGGAAGC TGACTTCTGG GGATTTTTT            147
Thr

TTTCCTCCAG AAAGACAAGC AACGTCCAT                                      176
```

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Arg Ala Val Thr Phe Pro Ala Ser Pro Val Glu Ala Arg Gln Ser Pro
1               5                  10                  15

Pro Leu Asn Arg Phe Asp Gly Tyr Glu Gly Ala Arg Pro Phe Pro Thr
            20                  25                  30
```